US012527682B2

(12) United States Patent
Sexton et al.

(10) Patent No.: US 12,527,682 B2
(45) Date of Patent: Jan. 20, 2026

(54) FECAL COLLECTION SYSTEMS AND METHODS

(71) Applicant: Sage Products LLC, Cary, IL (US)

(72) Inventors: Kristin M. Sexton, Cary, IL (US); Catherine S. Boulos, Vernon Hills, IL (US); Brian J. Ecklund, McHenry, IL (US); Medha Sesham, Aurora, IL (US); Justin L. vanHoozer, Acworth, GA (US)

(73) Assignee: Sage Products, LLC, Cary, IL (US)

( * ) Notice: Subject to any disclaimer, the term of this patent is extended or adjusted under 35 U.S.C. 154(b) by 279 days.

(21) Appl. No.: 18/121,905

(22) Filed: Mar. 15, 2023

(65) Prior Publication Data

US 2023/0293336 A1 Sep. 21, 2023

Related U.S. Application Data

(60) Provisional application No. 63/355,853, filed on Jun. 27, 2022, provisional application No. 63/319,790, filed on Mar. 15, 2022.

(51) Int. Cl.

*A61F 5/448* (2006.01)
*A61F 5/44* (2006.01)
*A61F 5/443* (2006.01)

(52) U.S. Cl.

CPC ............ *A61F 5/448* (2013.01); *A61F 5/4405* (2013.01); *A61F 5/443* (2013.01)

(58) Field of Classification Search

CPC .......... A61F 5/443; A61F 5/448; A61F 5/449; A61F 5/4405; A61F 5/4407; A61F 5/4408; A61F 2205/4407

See application file for complete search history.

(56) References Cited

U.S. PATENT DOCUMENTS 2,337,648 A 12/1943 Clarke
2,491,799 A 12/1949 Clarke
(Continued)

FOREIGN PATENT DOCUMENTS

AU 2021 261 028 A1 12/2022
CA 2369190 10/2000
(Continued)

OTHER PUBLICATIONS

International Search Report and the Written Opinion of the International Searching Authority for Int'l Appl. No. PCT/US2021/028956 dated Jul. 23, 2021 (15 Pages).
(Continued)

*Primary Examiner* — Philip R Wiest
(74) *Attorney, Agent, or Firm* — McDonnell Boehnen Hulbert & Berghoff LLP

(57) ABSTRACT

In an example, a fecal collection system includes a user interface assembly, a drainage conduit, and a collection reservoir. The user interface assembly includes a user interface and an applicator. The user interface has a proximal side and a distal side. The proximal side is configured to couple to skin of a user. The applicator is coupled to the distal side of the user interface. The applicator is removable from the user interface while the user interface is coupled to the user. The drainage conduit extends between a proximal end and a distal end. The proximal end is configured to couple to the distal side of the user interface. The drainage conduit defines a lumen configured to guide feces from the proximal end to the distal end. The collection reservoir coupled to the distal end of the drainage conduit.

20 Claims, 29 Drawing Sheets

(56) References Cited

U.S. PATENT DOCUMENTS

| | | | | |
|---|---|---|---|---|
| 2,910,208 | A | 10/1959 | Doyle | |
| 3,119,541 | A | 1/1964 | Lynn | |
| 3,180,528 | A | 4/1965 | Balint et al. | |
| 3,248,002 | A | 4/1966 | Song | |
| 3,292,626 | A | 12/1966 | Schneider | |
| 3,304,039 | A | 2/1967 | Edelman et al. | |
| 3,366,116 | A | 1/1968 | Huck | |
| 3,401,827 | A | 9/1968 | Messina | |
| 3,577,989 | A | 5/1971 | Anderson | |
| 3,734,096 | A | 5/1973 | Millenbach | |
| 4,183,444 | A | 1/1980 | English et al. | |
| 4,445,898 | A | 5/1984 | Jensen | |
| 4,784,656 | A | 11/1988 | Christian | |
| 4,790,834 | A | 12/1988 | Austin | |
| 5,000,748 | A | 3/1991 | Fenton | |
| 5,312,384 | A | 5/1994 | Temple | |
| 5,346,483 | A | 9/1994 | Thaxton, Sr. | |
| 5,384,174 | A | 1/1995 | Ward | |
| 5,421,827 | A | 6/1995 | Temple | |
| 5,593,397 | A * | 1/1997 | La Gro | A61F 5/443 604/355 |
| 5,695,484 | A | 12/1997 | Cox | |
| 5,951,532 | A | 9/1999 | Olsen | |
| 6,350,256 | B1 | 2/2002 | Palumbo | |
| 6,406,464 | B1 | 6/2002 | Palumbo | |
| 6,464,674 | B1 | 10/2002 | Palumbo | |
| 6,508,794 | B1 | 1/2003 | Palumbo et al. | |
| 6,551,292 | B1 | 4/2003 | D'Acchioli et al. | |
| 6,685,685 | B2 | 2/2004 | Sugita et al. | |
| 6,732,879 | B2 | 5/2004 | Hamann | |
| 6,733,482 | B1 * | 5/2004 | Coles | A61F 13/82 977/841 |
| 6,916,312 | B2 | 7/2005 | Kondo et al. | |
| 7,001,370 | B2 | 2/2006 | Kubalak et al. | |
| 7,766,931 | B2 | 8/2010 | Blurton | |
| 7,862,878 | B2 | 1/2011 | Stroebech et al. | |
| 7,927,320 | B2 | 4/2011 | Goldwasser et al. | |
| 8,430,855 | B2 | 4/2013 | Burgess et al. | |
| 8,480,640 | B2 | 7/2013 | Santimaw | |
| 8,668,678 | B2 | 3/2014 | Stroebech et al. | |
| 8,721,608 | B2 | 5/2014 | Bach et al. | |
| 8,979,813 | B2 | 3/2015 | Uveborn | |
| 9,233,019 | B2 | 1/2016 | Lykke et al. | |
| 9,271,863 | B2 | 3/2016 | Stroebech et al. | |
| 9,492,597 | B2 | 11/2016 | Shelley et al. | |
| 9,597,428 | B2 | 3/2017 | Stroebech et al. | |
| 10,076,439 | B2 | 9/2018 | Paley | |
| 10,159,378 | B1 | 12/2018 | Orban et al. | |
| 10,472,128 | B2 | 11/2019 | Ciarrocchi | |
| 10,486,871 | B2 | 11/2019 | Ramey | |
| 10,561,523 | B2 | 2/2020 | Kim | |
| 10,842,663 | B2 | 11/2020 | Stroebech et al. | |
| 10,893,974 | B2 | 1/2021 | Nyberg | |
| 11,051,970 | B2 | 7/2021 | Paley | |
| 11,311,406 | B2 | 4/2022 | Roszkowiak et al. | |
| 11,497,640 | B1 | 11/2022 | Blurton et al. | |
| 11,590,018 | B2 | 2/2023 | Uridil et al. | |
| 2002/0082570 | A1 | 6/2002 | Mishima et al. | |
| 2003/0045843 | A1 | 3/2003 | Kondo et al. | |
| 2003/0150050 | A1 | 8/2003 | Tanaka et al. | |
| 2003/0204177 | A1 * | 10/2003 | Sugita | A61F 5/451 604/327 |
| 2004/0002687 | A1 | 1/2004 | Burns et al. | |
| 2004/0087919 | A1 | 5/2004 | Tanaka et al. | |
| 2004/0122384 | A1 * | 6/2004 | Evangelista | A61F 5/443 977/841 |
| 2005/0010180 | A1 | 1/2005 | Wang et al. | |
| 2007/0005033 | A1 | 1/2007 | Ciok et al. | |
| 2008/0065032 | A1 * | 3/2008 | Palmieri | A61F 5/445 604/347 |
| 2009/0093784 | A1 | 4/2009 | Hansen et al. | |
| 2009/0148661 | A1 | 6/2009 | Stroebech et al. | |
| 2010/0168693 | A1 * | 7/2010 | Edvardsen | A61F 5/451 604/355 |
| 2010/0217215 | A1 * | 8/2010 | Lykke | A61F 5/4404 604/344 |
| 2010/0298789 | A1 | 11/2010 | Santimaw | |
| 2011/0137273 | A1 | 6/2011 | Mullejans et al. | |
| 2013/0090617 | A1 | 4/2013 | Uveborn | |
| 2013/0197459 | A1 | 8/2013 | Brezoczky | |
| 2013/0320018 | A1 | 12/2013 | Crosby et al. | |
| 2014/0276501 | A1 | 9/2014 | Cisko | |
| 2014/0323909 | A1 * | 10/2014 | Kim | A61B 5/4255 604/355 |
| 2015/0239618 | A1 | 8/2015 | Pellingra et al. | |
| 2015/0328437 | A1 | 11/2015 | Rageh | |
| 2016/0106570 | A1 | 4/2016 | Paley | |
| 2016/0235582 | A1 | 8/2016 | Moavenian | |
| 2017/0007439 | A1 | 1/2017 | Boksan | |
| 2018/0250156 | A1 | 9/2018 | Lam | |
| 2019/0224035 | A1 * | 7/2019 | Nielsen | A61F 5/443 |
| 2020/0138618 | A1 * | 5/2020 | Roszkowiak | A61F 5/441 |
| 2020/0360173 | A1 | 11/2020 | Uridil et al. | |
| 2021/0000632 | A1 * | 1/2021 | Nielsen | A61F 5/445 |
| 2021/0121317 | A1 | 4/2021 | Bronnimann et al. | |
| 2021/0274917 | A1 | 9/2021 | Rainey | |
| 2021/0330485 | A1 * | 10/2021 | Sexton | A61F 5/443 |
| 2021/0394977 | A1 | 12/2021 | Tanaka et al. | |
| 2022/0265463 | A1 | 8/2022 | Miller et al. | |
| 2022/0331143 | A1 * | 10/2022 | Barker | A61F 5/4407 |
| 2022/0362048 | A1 | 11/2022 | Oliphant | |

FOREIGN PATENT DOCUMENTS

| | | | |
|---|---|---|---|
| EP | 2803342 | | 7/2016 |
| GB | 2116849 | | 10/1983 |
| JP | 2008253584 | | 10/2008 |
| WO | 2008048856 | A2 | 4/2008 |
| WO | 2009021520 | A1 | 2/2009 |
| WO | 2014201121 | A1 | 12/2014 |
| WO | 2019179586 | A1 | 9/2019 |
| WO | 2020152598 | | 7/2020 |

OTHER PUBLICATIONS

International Search Report and Written Opinion prepared by the European Patent Office in International Application No. PCT/US2024/028012 dated Oct. 21, 2024.

International Search Report and the Written Opinion of the International Searching Authority for International Application No. PCT/US2023/064415 dated May 25, 2023 (14 Pages).

* cited by examiner

FECAL COLLECTION SYSTEMS AND METHODS

CROSS-REFERENCE TO RELATED APPLICATION

The present application claims the benefit of U.S. Provisional Application No. 63/319,790, filed Mar. 15, 2022 and U.S. Provisional Application No. 63/355,853, filed Jun. 27, 2022, the contents of which are hereby incorporated by reference in their entirety.

FIELD

The present disclosure generally relates to fecal collection devices and systems for collecting feces discharged from the body of a user and carrying the feces away from the body.

BACKGROUND

Under various circumstances, a user may have limited or impaired mobility such that ordinary bowel movement functions and processes are rendered difficult (or impossible). For example, a person may have impaired mobility due to a disability or may be bedridden due to an injury or illness. Also, for example, feces collection may be needed for monitoring purposes, such as for monitoring inputs and outputs in a clinical setting (e.g., in an intensive care unit, or for other clinical and/or laboratory testing).

Various approaches have been developed to address some of the problems or circumstances related to impaired or restricted bowel movement processes. However, prior approaches suffer from problems or limitations of their own.

SUMMARY

In an example, a fecal collection system is described. The fecal collection system includes a user interface assembly, a drainage conduit, and a collection reservoir. The user interface assembly includes a user interface and an applicator. The user interface has a proximal side and a distal side. The proximal side is configured to couple to skin of a user. The applicator is coupled to the distal side of the user interface. The applicator is removable from the user interface while the user interface is coupled to the user. The drainage conduit extends between a proximal end and a distal end. The proximal end is configured to couple to the distal side of the user interface. The drainage conduit defines a lumen configured to guide feces from the proximal end to the distal end. The collection reservoir is coupled to the distal end of the drainage conduit.

In another example, a method of using a fecal collection system is described. The method includes positioning a user interface assembly at an anus of a user. The user interface assembly includes a user interface and an applicator. The method also includes coupling the user interface to the skin of the user by using the applicator to press the user interface against the skin of the user. The method further includes, after coupling the user interface to the skin of the user, removing the applicator from the user interface.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

Figure 1:
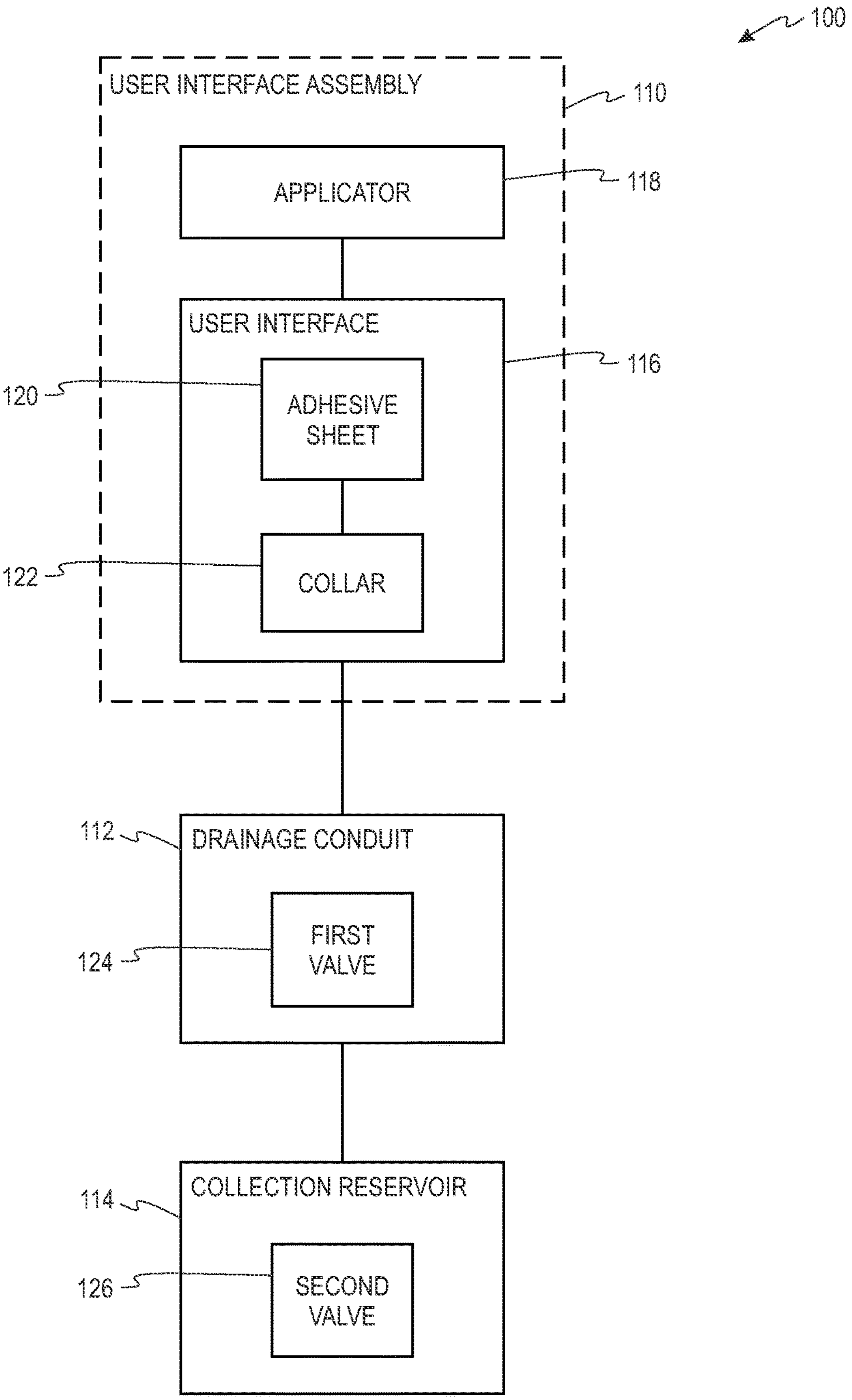
FIG. 1 illustrates a simplified block diagram of a fecal collection system, according to an example.

Referring to FIG. 1, a simplified block diagram of a fecal collection system 100 is shown according to an example. As shown in FIG. 1, the fecal collection system 100 includes a user interface assembly 110, a drainage conduit 112, and a collection reservoir 114. The fecal collection system 100 can be coupled to the skin of the user such that the fecal collection system 100 is external to the body of the user.

The user interface assembly 110 includes a user interface 116 and an applicator 118. The user interface 116 has a proximal side and a distal side. The proximal side is configured to couple to the skin of a user. For instance, the user interface 116 can include an adhesive sheet 120 on the proximal side. As one example, the adhesive sheet 120 can include a biocompatible adhesive such as, for instance, a silicon adhesive that can provide for coupling the user interface 116 to the skin of the user. In one example, the adhesive sheet 120 can be configured to couple the user interface 116 to the user's skin for a period of at least eight hours before being removed and/or replaced. In another example, the adhesive sheet 120 can be configured to couple the user interface 116 to the user's skin for a period of approximately 12 to 72 hours before being removed and/or replaced.

The applicator 118 is coupled to the distal side of the user interface 116. The applicator 118 is removable from the user interface 116 while the user interface 116 is coupled to the user. In this arrangement, the applicator 118 can assist in coupling the user interface 116 to the skin of the user, and then be removed to provide for coupling the drainage conduit 112 to the user interface 116 and/or reduce an amount of material of the fecal collection system 100 between the user and a support structure (e.g., a hospital bed and/or wheel chair). Removing the applicator 118 can thus help to mitigate a risk of pressure sores.

The drainage conduit 112 extends between a proximal end and a distal end. In one example, the proximal end of the drainage conduit 112 can be fixedly coupled to the distal side of the user interface 116 before the applicator 118 is removed from the user interface 116. In this example, the drainage conduit 112 can be coupled to the user interface 116 while the user interface 116 is being coupled to the skin of the user. In another example, the proximal end is configured to couple to the distal side of the user interface 116 after the applicator 118 is removed from the user interface 116. More generally, the drainage conduit 112 defines a lumen configured to guide feces from the proximal end to the distal end. The collection reservoir 114 coupled to the distal end of the drainage conduit 112. The collection reservoir 114 is configured to contain the feces.

The drainage conduit 112 and the lumen can have an elongated shape. In an example, the drainage conduit 112 can have a length of approximately 4 feet to approximately 6 feet. This length can help to position the collection reservoir 114 at a location that is remote from the user (e.g., at a side of a patient support structure such as a hospital bed). However, the drainage conduit 112 can have a different length in other examples.

Additionally, in some examples, the drainage conduit 112 can be configured to guide the feces from the proximal end to the distal end responsive to milking the drainage conduit 112 toward the collection reservoir 114 (e.g., by applying compression to the drainage conduit 112 along a length of drainage conduit 112 in a direction from the proximal end to the distal end). For instance, the drainage conduit 112 can have a hardness and/or a pliability that facilitates manually milking the feces toward the collection reservoir 114. Also, as examples, the drainage conduit 112 can be formed from a polyurethane (PU) and/or a polyvinyl chloride (PVC). For instance, the drainage conduit 112 can be a film tube having a thickness between approximately 2 mil and approximately 4 mil.

In some implementations, the drainage conduit 112 can be at least partially transparent or translucent. This can help to determine whether feces is present in the drainage conduit 112 such that a determination can be made to milk the drainage conduit 112 and force the feces to the collection reservoir 114.

In an alternative example, the fecal collection system 100 can omit the drainage conduit 112 such that the collection reservoir 114 is directly coupled to the user interface 116. Although this may reduce a cost of manufacture and reduce a need to milk the drainage conduit 112, the collection reservoir 114 is positioned nearer to the user, which increases a bulk of the device that may contact the user and makes replacing the collection reservoir 114 more challenging.

As noted above, the user interface 116 can include the adhesive sheet 120. The adhesive sheet 120 can define an aperture in communication with the lumen of drainage conduit 112. In this arrangement, feces can pass from an anus of the user into the drainage conduit 112 through the aperture of the adhesive sheet 120. The drainage conduit 112 can then guide the feces to the collection reservoir 114.

In one example, the aperture of the adhesive sheet 120 can have a diameter of approximately 1.5 inches. This can help to provide a sufficiently large opening to receive the feces into the drainage conduit 112 while allowing for a surface area of the adhesive sheet 120 to secure the fecal collection system 100 to the skin of the user. In another example, the aperture of the adhesive sheet 120 can have a diameter of approximately 1 inch to approximately 2 inches.

In some implementations, the user interface 116 can also include a collar 122 extending distally from the adhesive sheet 120. As described above, the adhesive sheet 120 can include an adhesive such as, for example, a silicon adhesive that can provide for coupling the user interface 116 to the skin of the user. The proximal end of the drainage conduit 112 can be coupled to the collar 122 of the user interface 116. For example, the collar 122 can be a foam wedge and can be received at the proximal end of the drainage conduit 112. In this example, the collar 122 can thus couple to the drainage conduit 112 by friction-fit connection. However, in other examples, the collar 122 can additionally or alternatively couple to the drainage conduit 112 by a threaded connection, a hook and loop connection, and/or an adhesive connection.

More generally, the collar 122 can be configured to provide for coupling, decoupling, and/or recoupling one or more drainage conduits 112 to the user interface 116. As such, the collar 122 can provide for changing the drainage conduit 112 and/or the collection reservoir 114 without removing the user interface from 116 from the user. For instance, a method of using the fecal collection system 100 can include removing a first drainage conduit 112 from the user interface 116 after an initial period of use (e.g., approximately 8 hours) and then coupling a second drainage conduit 112 to the user interface 116.

In an example, the collar 122 can define a first aperture in communication with the lumen of drainage conduit 112, and the adhesive sheet 120 can define a second aperture that is axially aligned with the first aperture of the collar 122. In this arrangement, feces can pass from an anus of the user into the drainage conduit 112 through the first aperture of the collar 122 and the second aperture of the adhesive sheet 120. The drainage conduit 112 can then guide the feces to the collection reservoir 114.

In one example, the first aperture and the second aperture can have a diameter of approximately 1.5 inches. This can help to provide a sufficiently large opening to receive the feces into the drainage conduit 112 while allowing for a surface area of the adhesive sheet 120 to secure the fecal collection system 100 to the skin of the user. In another example, the first aperture and/or the second aperture can have a diameter of approximately 1 inches to approximately 2 inches.

In an example, the fecal collection system 100 can also include a first one-way valve 124 in the lumen defined by the drainage conduit 112. The first one-way valve 124 is configured to allow feces to flow in a direction from the proximal end to the distal end of the drainage conduit 112 and inhibit the feces from flowing in a direction from the distal end to the proximal end of the drainage conduit 112. This can help inhibit feces from migrating back toward and into contact with the skin of the user.

In one example, the first one-way valve 124 can be configured to transition from a closed state to an open state responsive to feces passing through the first one-way valve 124 in a distal direction (e.g., from the user toward the drainage conduit 112). In the closed state, the first one-valve 124 can inhibit backflow of feces in a proximal direction toward the user (e.g., toward the user interface assembly 110). In the open state, the first one-way valve 124 can expand to define an enlarged passageway that allows the feces to pass through the first one-way valve 124 in a distal direction. In one implementation, the first one-way valve 124 can be configured to expand to have a diameter that is approximately equal to a diameter of the drainage conduit 112. For instance, in an implementation in which the drainage conduit 112 has a diameter of approximately 1.5 inches, the first one-way valve 124 can expand from a diameter of approximately zero inches in the closed state to a diameter of approximately 1.5 inches in the open state.

In one example implementation, the first one-way valve 124 can include a plurality of flaps that extend distally from a proximal end of the drainage conduit 112 (e.g., at the aperture of the adhesive sheet 120). In this arrangement, the flaps can taper towards each other along a length of the flaps in a direction from the proximal end of the drainage conduit 112 toward a distal end of the drainage conduit 112. In one example, a material of the flaps can be the same as a material of the drainage conduit 112. The flaps can a monolithic structure (e.g., integral) with the drainage conduit 112 or the flaps can be distinct structures coupled to the drainage conduit 112 (e.g., via a weld).

The collection reservoir 114 can additionally or alternatively include a second one-way valve 126 that is configured to allow feces to flow from the drainage conduit 112 to the collection reservoir 114 and inhibit the feces from flowing from the collection reservoir 114 to the drainage conduit 112. This can also help inhibit feces from migrating back toward and into contact with the skin of the user. In one example, the drainage conduit 112 can have a diameter of approximately 1 inch to approximately 3 inches at the distal end 212B.

Figure 2:
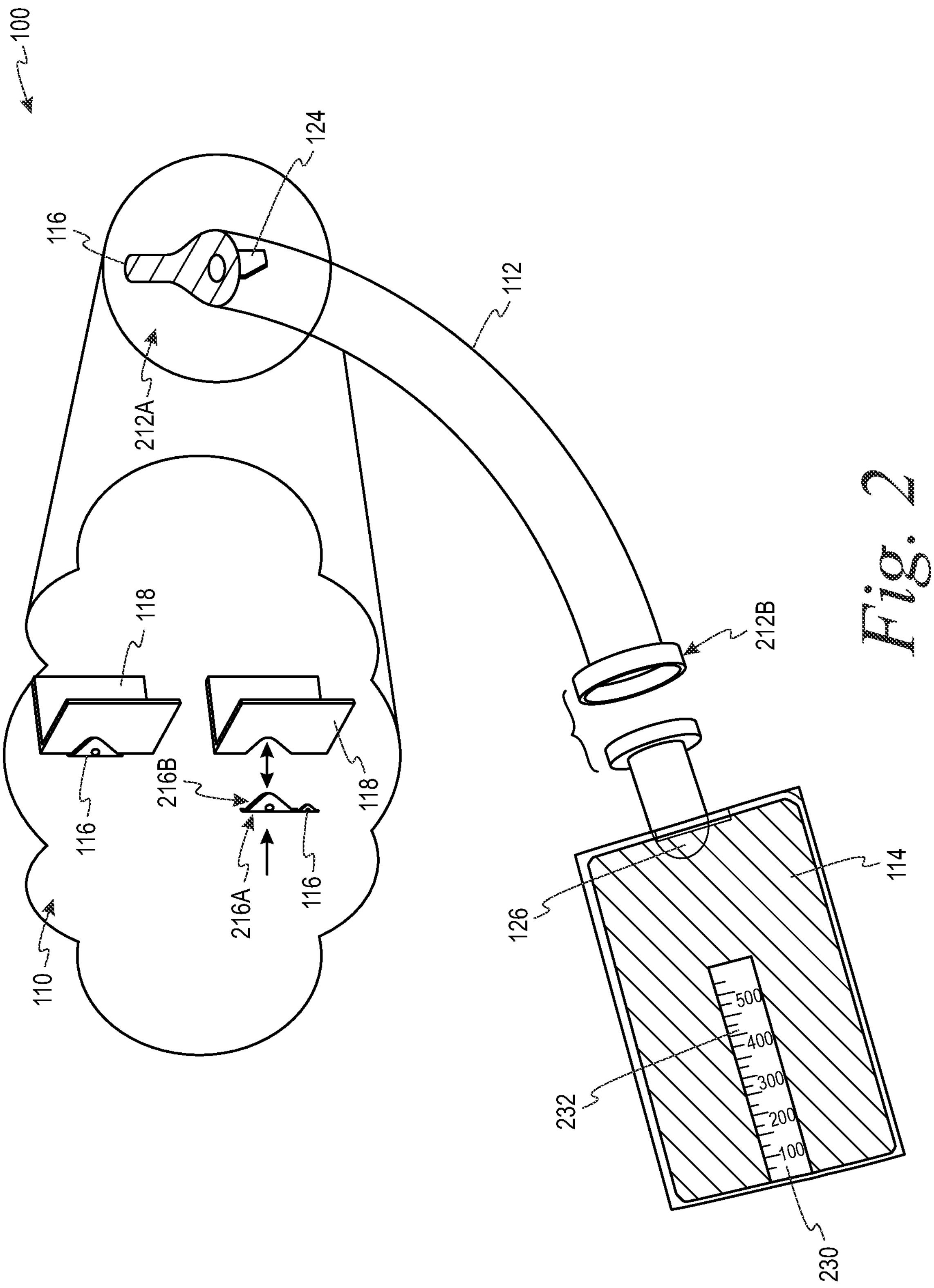
FIG. 2 illustrates an implementation of the fecal collection system shown in FIG. 1, according to an example.

FIG. 2 depicts an implementation of the fecal collection system 100 according to an example. As shown in FIG. 2, the fecal collection system 100 includes the user interface assembly 110, the drainage conduit 112, and the collection reservoir 114 as described above. As described above, the user interface assembly 110 includes the user interface 116 having a proximal side 216A and a distal side 216B. Additionally, in FIG. 2, the drainage conduit 112 extends between a proximal end 212A and a distal end 212B.

As shown in FIG. 2, the drainage conduit 112 can be configured to be coupled, decoupled, and re-coupled to the collection reservoir 114. This can provide for decoupling a first collection reservoir 114 containing feces, and coupling a second collection reservoir 114 that is empty to continue collecting feces without having to decouple the user interface 116 and/or the drainage conduit 112 from the skin of the user. In some examples, the drainage conduit 112 and the collection reservoir 114 can be coupled, decoupled, and recoupled to the user interface 116 while the user interface 116 remains coupled to the skin of the user. This can provide for changing the drainage conduit 112 and/or the collection reservoir 114 without removing the user interface from 116 from the user. In other examples, the drainage conduit 112 can be permanently fixed to the collection reservoir 114. This can help to mitigate a risk of leakage at an interface between the user interface 116 and the drainage conduit 112.

Additionally, as shown in FIG. 2, the collection reservoir 114 can include a measurement window 230 including a plurality of volumetric markings 232. The measurement window 230 can be at least one of transparent or translucent such that a quantity of feces in the collection reservoir 114 can be visually observed. This can provide an indication when the collection reservoir 114 should be changed, and/or when sufficient volume of feces has been collected to provide a sample for a diagnostic evaluation.

In FIG. 2, the first one-way valve 124 is positioned at the proximal end 214A. In other examples, the first one-way valve 124 can be positioned between the proximal end 214A and the distal end 214B of the drainage conduit 112.

Figure 3A:
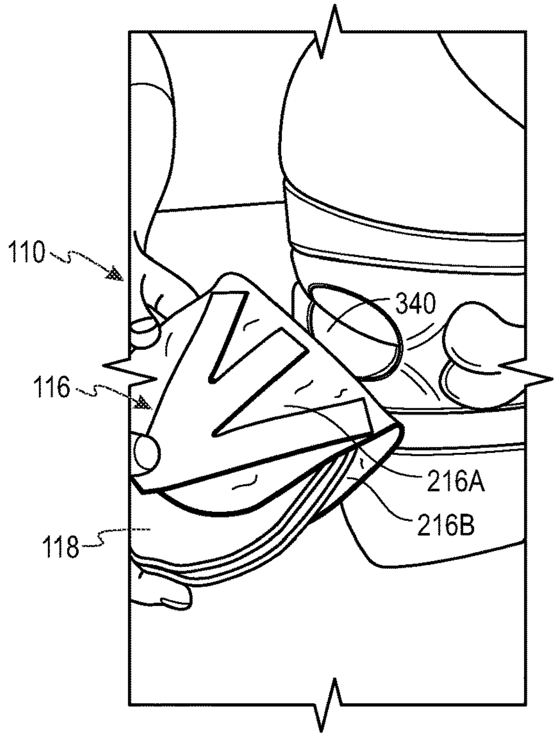
FIGS. 3A-3D illustrate a process for coupling a user interface assembly to the skin of a user according to one example implementation of the user interface assembly shown in FIG. 1.

FIGS. 3A-3D depict a process for coupling the user interface assembly 110 to the skin of a user according to one example implementation of the user interface assembly 110. As shown in FIGS. 3A-3D, the user interface assembly 110 includes the user interface 116 and the applicator 118. In FIG. 3A, the user interface assembly 110 is positioned at an anus 340 of the user. The user interface assembly 110 is folded such that the proximal side 216A of the user interface 116 faces outward, and the distal side 216B of the user interface 116 faces inward.

Figure 3B:
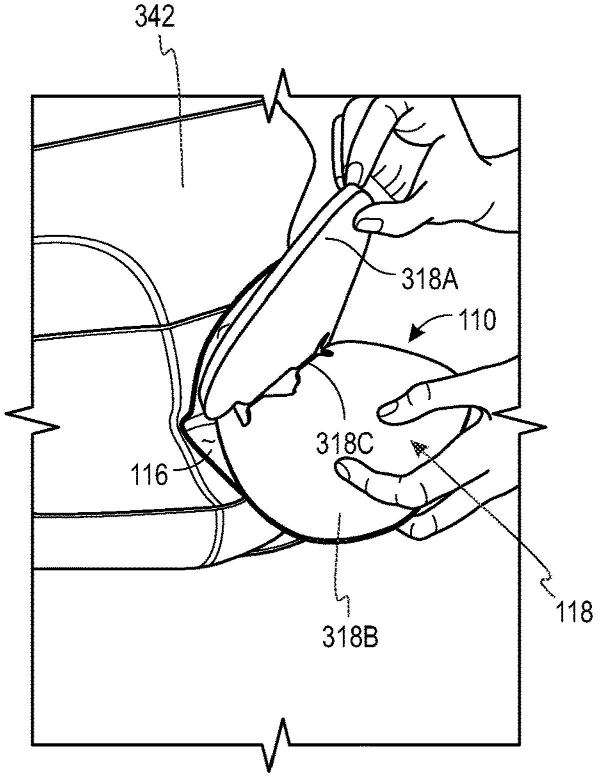

In FIG. 3B, the applicator 118 is used to press the proximal side 216A of the user interface 116 against the skin 342 of the user. In this example, the applicator 118 includes a first lateral portion 318A and a second lateral portion 318B that are hingedly movable relative to each other. For instance, the applicator 118 can include a hinged portion 318D between the first lateral portion 318A and the second lateral portion 318B. In this example, the hinged portion 318C is perforated to assist in removing the applicator 118 from the user interface 116. As shown in FIG. 3B, the first lateral portion 318A of the applicator 118 and a second lateral portion 318B of the applicator 118 can be moved relative to each other to press the user interface 116 against the skin 342 of the user.

Figure 3C:
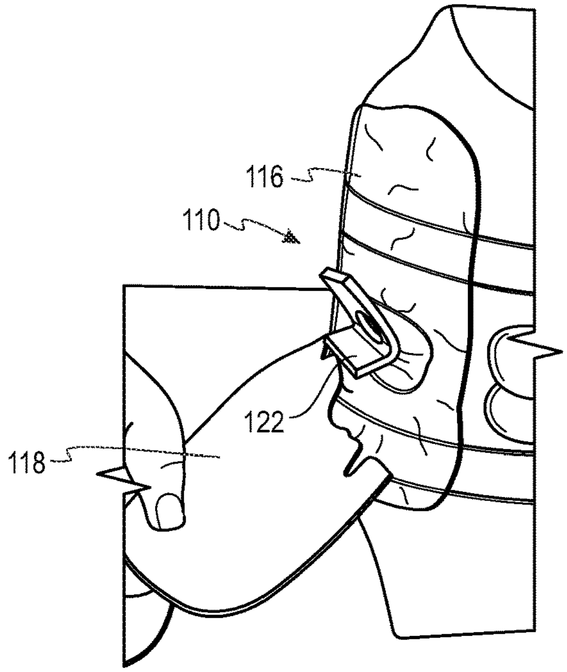
Figure 3D:
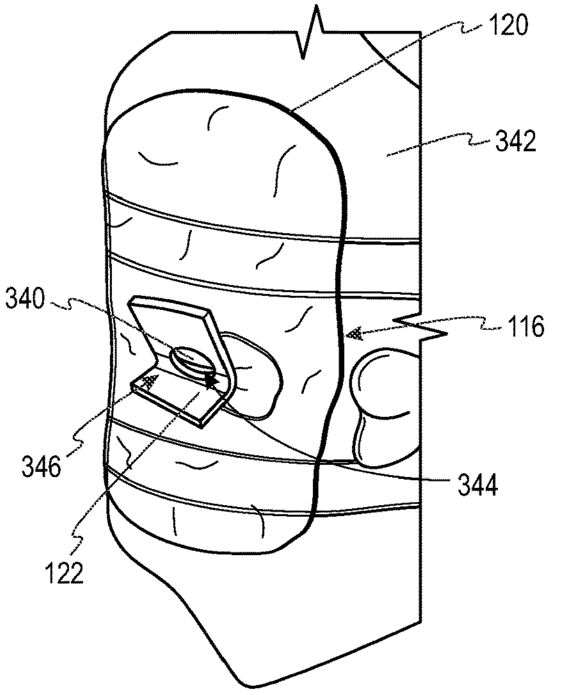

In FIG. 3C, the applicator 118 is being removed from the user interface 116. For example, the applicator 118 can be removed from the user interface 116 by decoupling the first lateral portion 318A and the second lateral portion 318B from the user interface 116 along the perforation line of the hinged portion 318C. As shown in FIGS. 3C-3D, the removing the applicator 118 can expose the collar 122 of the user interface 116. In FIG. 3D, the user interface 116 is coupled to the skin 342 of the user. As shown in FIG. 3D, the adhesive sheet 120 is coupled to the skin 342 and the collar 122 extends distally from the adhesive sheet 120. Also, in FIG. 3D, the collar 122 defines a first aperture 344, the adhesive sheet 120 defines a second aperture 346, and the first aperture 344 and the second aperture 346 are aligned with the anus 340 of the user.

Figure 4:
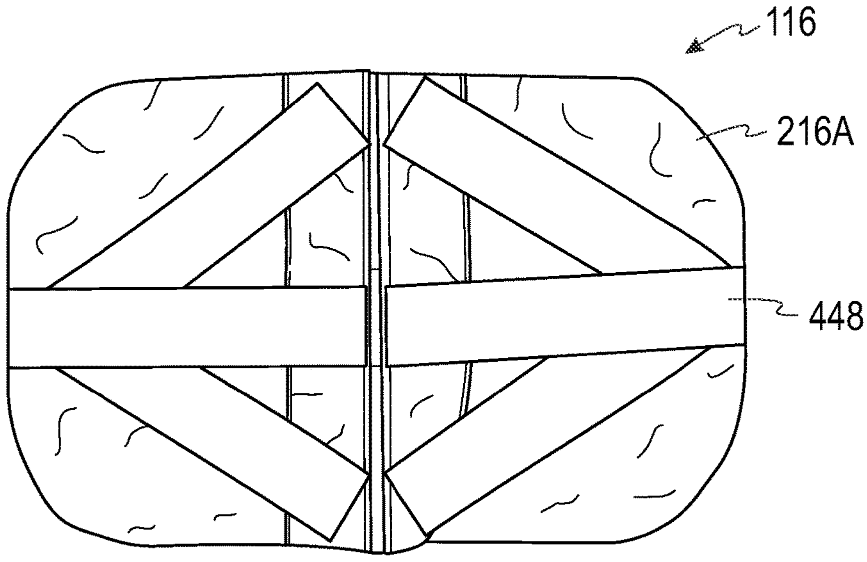
FIG. 4 illustrates a proximal side of the user interface according to an example.

FIG. 4 depicts the proximal side 216A of the user interface 116 according to an example. In FIG. 4, the user interface 116 includes a release liner 448 that covers and adhesive on the proximal side 216A of the user interface 116. The release liner 448 can be removed to expose the adhesive prior to coupling the user interface 116 to the skin of the user.

Figure 5:
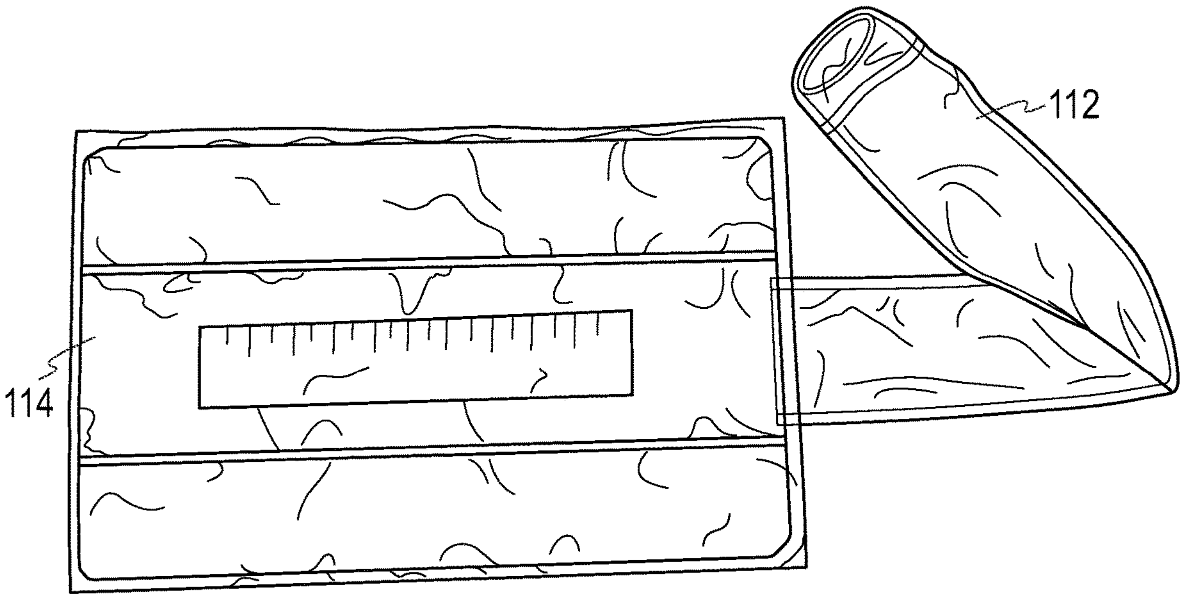
FIG. 5 illustrates a drainage conduit and a collection reservoir according to an example.

FIG. 5 depicts the drainage conduit 112 and the collection reservoir 114 according to an example implementation.

Figure 6:
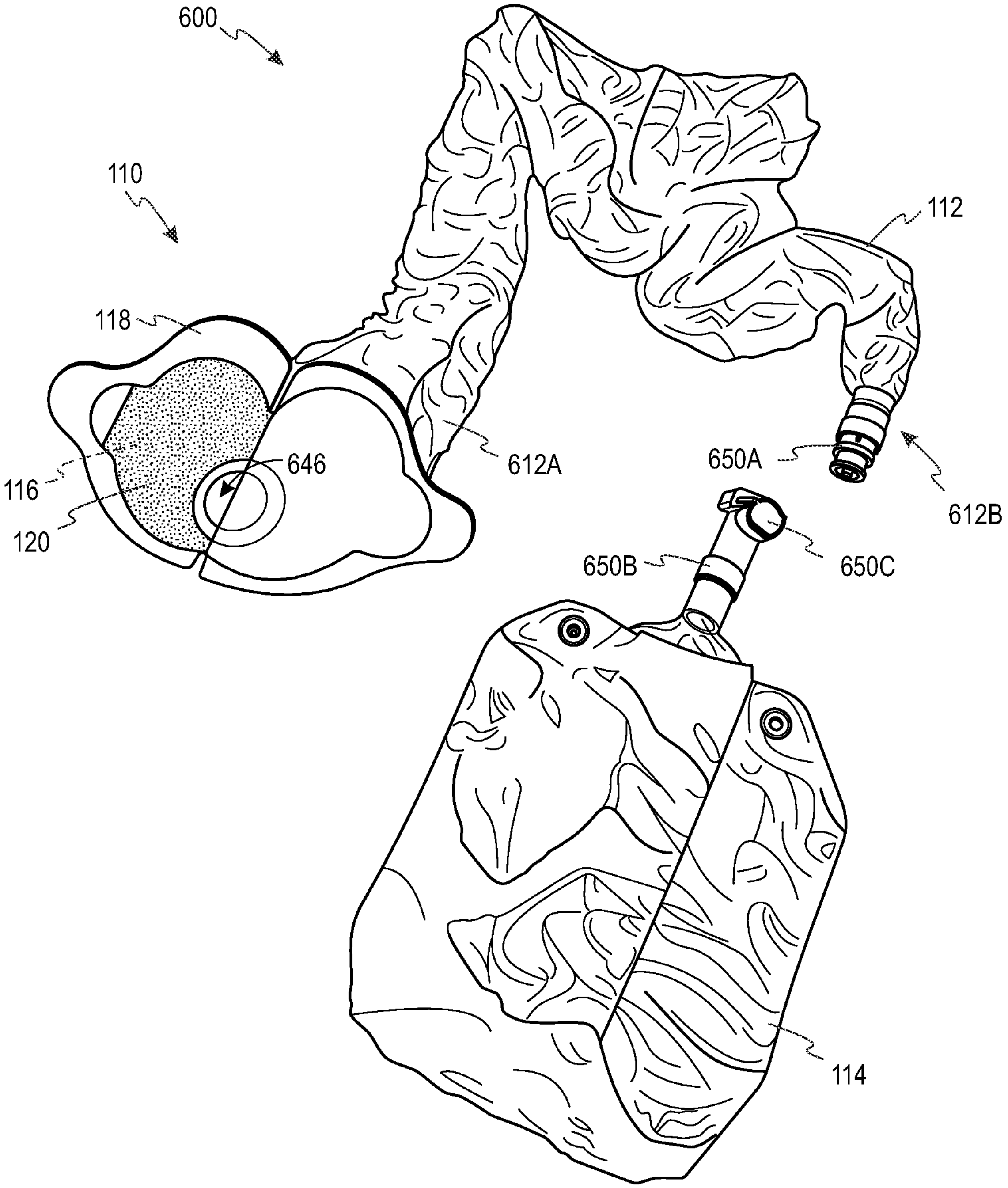
FIG. 6 illustrates an implementation of the fecal collection system shown in FIG. 1, according to another example.

Referring now to FIG. 6, a fecal collection system 600 is depicted for an implementation of the fecal collection system 100 according to another example. As shown in FIG. 6, the fecal collection system 600 includes the user interface assembly 110, the drainage conduit 112, and the collection reservoir 114 as described above. As described above, the user interface assembly 110 includes the user interface 116 having a proximal side and a distal side. Additionally, in FIG. 6, the drainage conduit 112 extends between a proximal end 612A and a distal end 612B.

As shown in FIG. 6, the drainage conduit 112 can be configured to be coupled, decoupled, and re-coupled to the collection reservoir 114. This can provide for decoupling a first collection reservoir 114 containing feces, and coupling a second collection reservoir 114 that is empty to continue collecting feces without having to decouple the user interface 116 from the skin of the user. In other examples, the drainage conduit 112 can be permanently fixed to the collection reservoir 114. In such examples, the drainage conduit 112 and the collection reservoir 114 can be coupled, decoupled, and recoupled to the user interface 116 while the user interface 116 remains coupled to the skin of the user (e.g., in other examples, the user interface 110 can further include the collar 122 described above).

In FIG. 6, the distal end 612B of the drainage conduit 112 includes a male quick-connect coupler 650A that can couple to a female quick-connect coupler 650B of the collection reservoir 114. The female quick-connect coupler 650B of the collection reservoir 114 further includes an actuator 650C (e.g., a button) that is operable to couple and/or decouple the male quick-connect coupler 650A and the female quick-connect coupler 650B to each other. In this arrangement, the drainage conduit 112 can remain securely coupled to the collection reservoir 114 until the actuator 650C is operated to decouple the male quick-connect coupler 650A of the drainage conduit 112 from the female quick-connect coupler 650B of the collection reservoir 114. This can help to inhibit (or prevent) inadvertent decoupling of the drainage conduit 112 and the collection reservoir 114. Although the drainage conduit 112 includes the male quick-connect coupler 650A and the collection reservoir 114 includes the female quick-connect coupler 650B in FIG. 6, the drainage conduit 112 can include the female quick-connect coupler 650B and the collection reservoir 114 can include the male quick-connect coupler 650A in an alternative example.

Additionally, as described above, the collection reservoir 114 can include a measurement window including a plurality of volumetric markings (e.g., similar to the collection reservoir 114 shown in FIGS. 2 and 5). The measurement window can be at least one of transparent or translucent such that a quantity of feces in the collection reservoir can be visually observed. This can provide an indication when the collection reservoir should be changed, and/or when sufficient volume of feces has been collected to provide a sample for a diagnostic evaluation.

In FIG. 6, the proximal end 612A of the drainage conduit 112 is coupled to the distal side of the user interface 116. In this example, the drainage conduit 112 can be non-removably coupled (e.g., fixedly and permanently coupled) to the user interface 116. For instance, the proximal end 612A of the drainage conduit 112 can be welded to the adhesive sheet 120 at an aperture 646 in the adhesive sheet 120.

Figure 7:
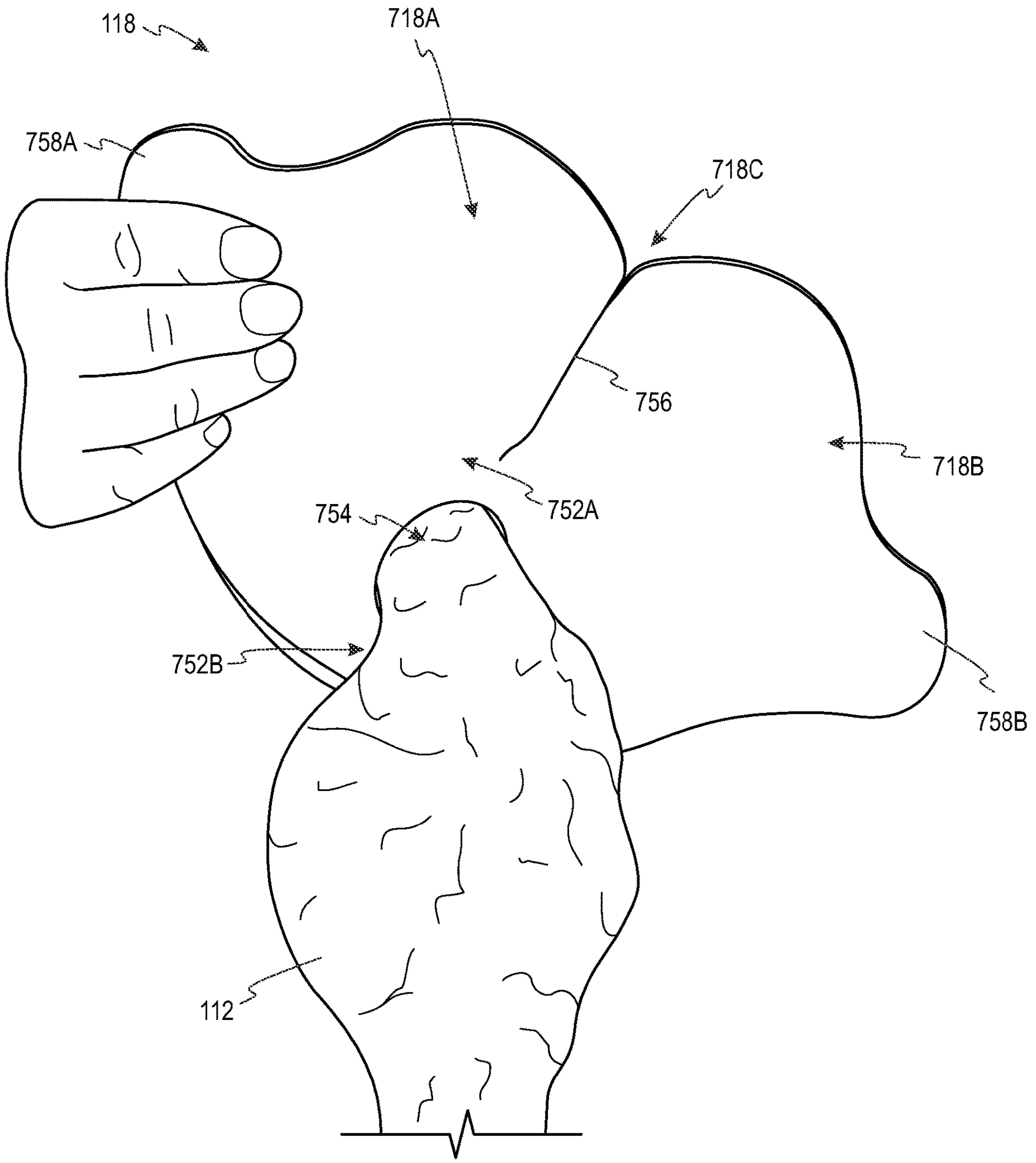
FIG. 7 illustrates a distal side of an applicator for the fecal collection system shown in FIG. 6, according to an example.
Figure 8A:
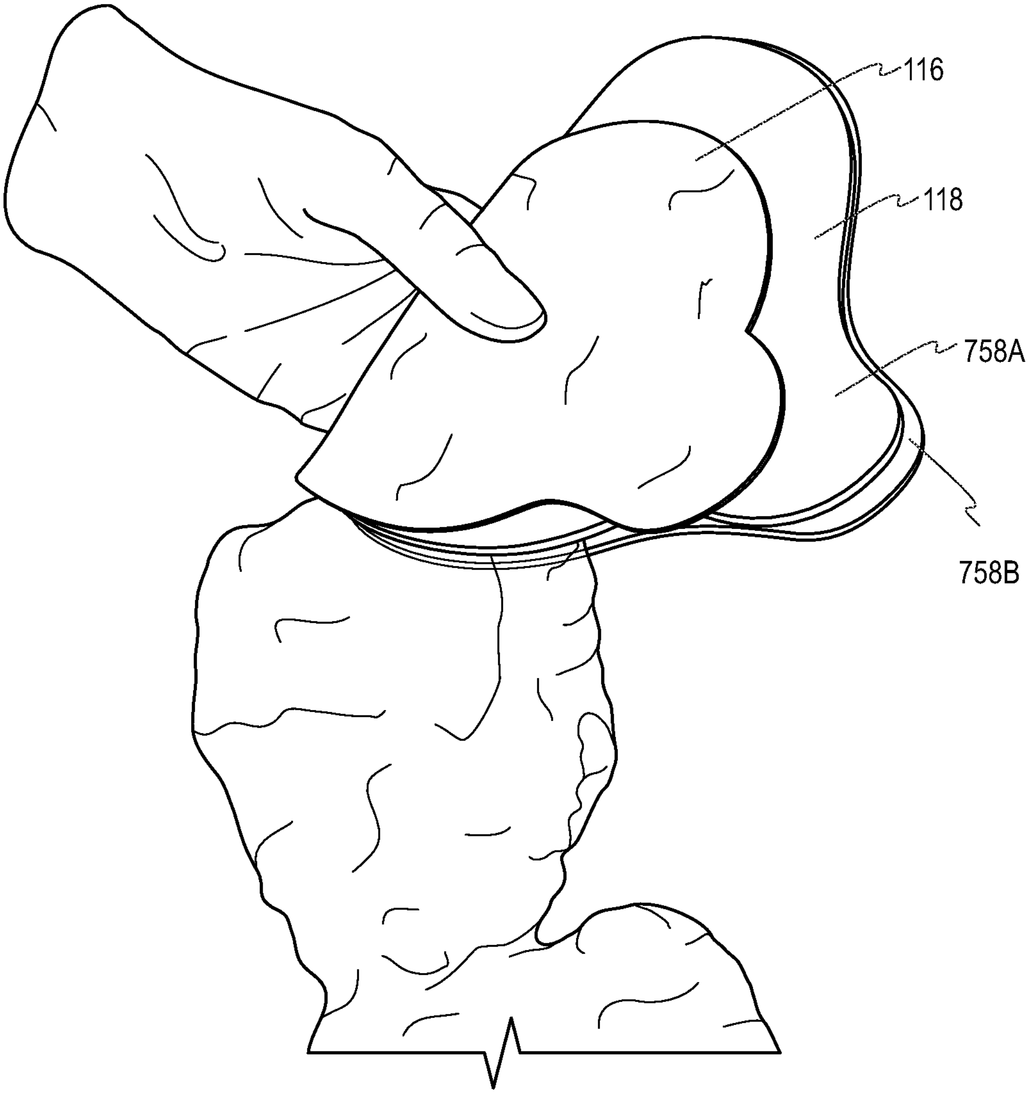
FIG. 8A illustrates the user interface in a folded state for the fecal collection system shown in FIG. 6, according to an example.
Figure 8B:
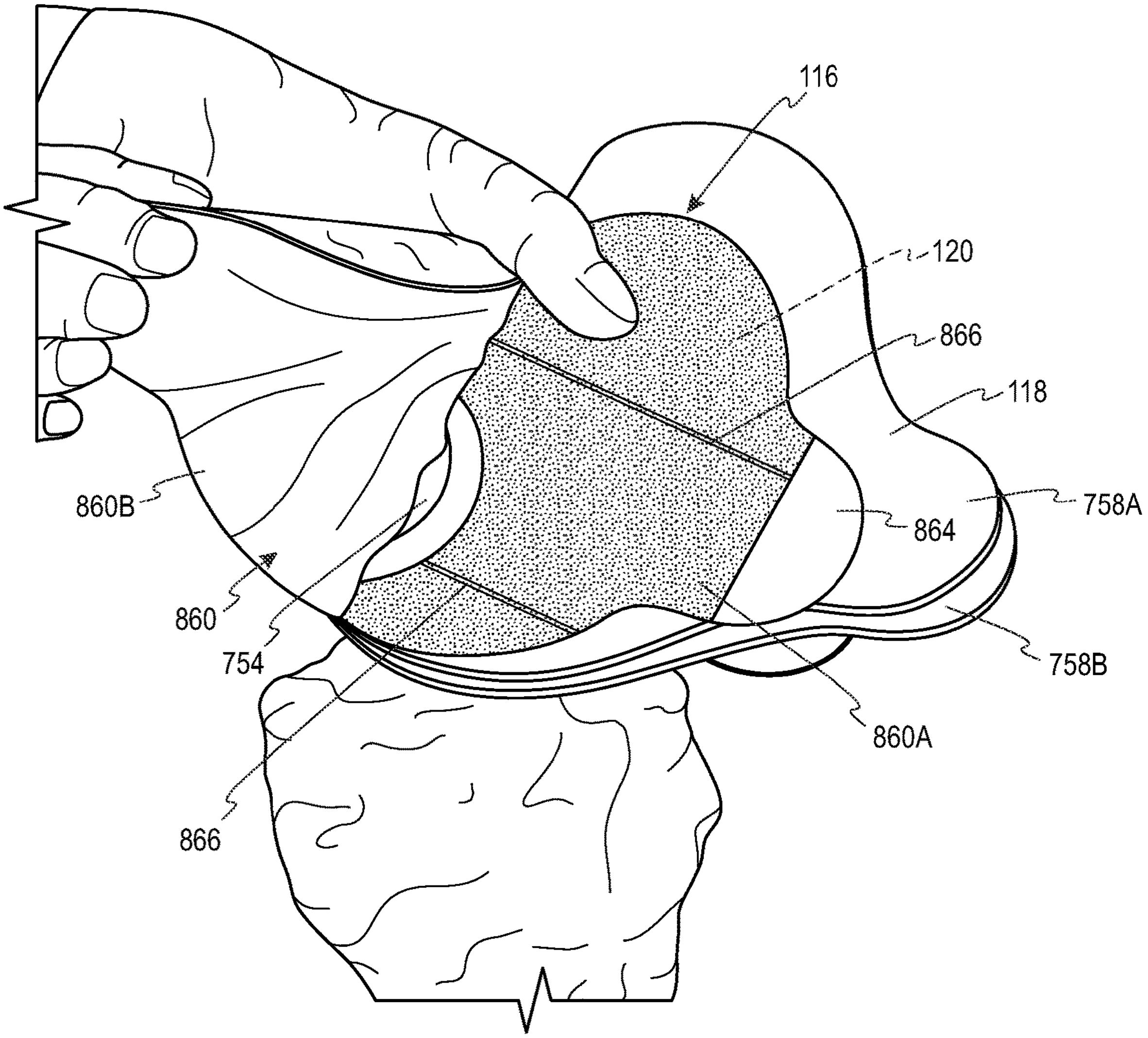
FIG. 8B illustrates the user interface for the fecal collection system shown in FIG. 6, according to an example.

FIG. 7 depicts the applicator 118 according to the example shown in FIG. 6. As shown in FIG. 7, the applicator 118 includes a first lateral portion 718A, a second lateral portion 718B, and a hinge portion 718C between the first lateral portion 718A and the second lateral portion 718B. In this arrangement, the first lateral portion 718A and the second lateral portion 718B are configured to move about the hinge portion 718C between an extended state (as shown in FIG. 7) and a folded state (as shown in FIGS. 8A-8B). As described below, the folded state can help to insert the applicator 118 and the user interface 116 between buttocks to access an anus of a user. The extended state can help remove the applicator 118 from the user interface 116, as described above.

The hinge portion 718C is further configured to facilitate removing the applicator 118 from the user interface 116. For example, in FIG. 7, the hinge portion 718C includes a first bridge portion 752A and a second bridge portion 752B connecting the first lateral portion 718A of the applicator 118 to the second lateral portion 718B of the applicator 118 (e.g., the first later portion 718A and the second lateral portion 718B can be coupled to each other only at the first bridge portion 752A and the second bridge portion 752B). The first bridge portion 752A and the second bridge portion 752B can have a size that is relatively small compared to an overall size of the applicator 718 in a dimension extending along an intersection between the first lateral portion 718A and the second lateral portion 718B. For instance, a combined length of the first bridge portion 752A and the second bridge portion 752B can be less than approximately 50 percent of an overall length of the applicator 118 in this dimension. This relative size can provide for (i) inhibiting inadvertent separation of the first lateral portion 718A and the second lateral portion 718B during coupling of the user interface 116 to the user and (ii) easily tearing the first lateral portion 718A and the second lateral portion 718B apart from each other after coupling the user interface 116 to the user.

In some implementations, the first bridge portion 752A and/or the second bridge portion 752B can include perforations to assist in decoupling the first lateral portion 718A and the second lateral portion 718B from each other. The perforations can allow for the combined length of the first bridge portion 752A and the second bridge portion 752B to be greater than approximately 50 percent of an overall length of the applicator 118 in the dimension extending along an intersection between the first lateral portion 718A and the second lateral portion 718B (e.g., along the hinge portion 718C).

Additionally, as shown in FIG. 7, the drainage conduit 112 extends through an aperture 754 in the applicator 118. The first bridge portion 752A is defined between the aperture 754 and a slit 756, which extends along the hinge portion 718C between the first lateral portion 718A and the second lateral portion 718B of the applicator 718. The slit 756 can help to reduce a size of the first bridge portion 752A relative to the overall size of the applicator 718 along the interface between the first lateral portion 718A and the second lateral portion 718B. The slit 756 can additionally or alternatively help to enhance the movability of the first lateral portion 718A and the second lateral portion 718B about the hinge portion 752C.

In one example, the slit 756 can have a length that is greater than approximately 40 percent of the overall length of the applicator 118 in the dimension extending along the hinge portion 718C (e.g., a dimension through the first bridge portion 752A, the aperture 754, and the second bridge portion 752B). This can help to achieve the functionalities of the slit 756 described above.

The second bridge portion 752B can be defined between the aperture 754 (e.g., at a point that is opposite the first bridge portion 752A) and a peripheral edge of the applicator 118 at the hinge portion 718C. As shown in FIG. 7, the aperture 754 can be at a location that is offset from a center of the applicator 118. More particularly, the aperture 754 can be at position that is closer to a lower edge of the applicator 118 than an upper edge of the applicator 118. As such, the proximal end of the drainage conduit 112 can be coupled to the user interface 116 at a location that is offset below a center of the user interface 116. This can help to apply the user interface 116 at the anus of the user, which is generally located at a position that is below a center of the user's buttocks.

As shown in FIG. 7, the applicator 118 can further include a first tab 758A on a peripheral edge of the first lateral portion 718A and a second tab 758B on a peripheral edge of the second lateral portion 718B. The first tab 758A and the second tab 758B can extend laterally past a peripheral edge of the user interface 116 such that the first tab 758A and the second tab 758B can facilitate gripping and handling of the applicator 118 when positioning the user interface assembly 110 between a user's buttocks.

FIGS. 8A-8B depict the user interface 116 and the applicator 118 in the folded state such that the first lateral portion 718A and the second lateral portion 718B are folded about the hinge portion 718C, and the user interface 116 is positioned externally to the applicator 118. As shown in FIG. 8A, the applicator 118 can have a size that is larger than the user interface 116 (e.g., the first tab 758A and the second tab 758B can extend past a peripheral edge of the user interface 116). This can help provide access to the applicator 118. In another example, the applicator can have a size that is approximately equal to a size of the user interface 116. More generally, the user interface 116 and the applicator 118 can be configured to provide for holding the user interface 116 and the applicator 118 in a single hand while the user interface 116 and the applicator 118 are in a folded state.

In FIGS. 8A-8B, the user interface 116 includes the adhesive sheet 120 (shown in FIG. 8B), a first release liner 860, and a second release liner (not shown in FIGS. 8A-8B). The first release liner 860 is removably coupled to a first half of the adhesive sheet 120 (e.g., on a first side of the hinge portion 718C and the aperture 754 in FIGS. 8A-8B), and the second release liner is removably coupled to a second half of the adhesive sheet 120 (e.g., on a second side of the hinge portion 718C and the aperture 754 in FIGS. 8A-8B). In this arrangement, the first release liner 860 and the second release liner can be independently removed from the adhesive sheet 120 to provide for coupling the user interface 116 to the user's skin on one side at a time.

The first release liner 860 can include a first portion 860A and a second portion 860B. The first portion 860A can cover the first half of the adhesive sheet 120 to inhibit the adhesive sheet 120 prematurely or inadvertently adhering to an object prior to application of the user interface 116 to the user. The second portion 860B can have a first end that is coupled to the first portion 860A at an inner portion of the user interface 116 (e.g., at the aperture 754), and a second end that is separate from the first portion 860A at an outer portion of the user interface 116 (e.g., at the peripheral edge of the user interface 116). In this arrangement, a practitioner can grasp the second end at the periphery of the user interface 116 and pull outwardly away from the user to separate the first portion 860A of the first release liner 860 from the adhesive sheet 120. In this way, the first release liner 860 can be progressively expose the first half the adhesive sheet 120 in a direction from the aperture 754 towards the peripheral edge of the user interface 116. This can help to improve coupling the adhesive sheet 120 to the buttocks of the user with the aperture 754 aligned with the anus of the user.

Although not shown in FIGS. 8A-8B, the second release liner can be arranged in a similar manner with respect to the second half of the adhesive sheet 120. As such, the second release liner can include a first portion and a second portion. The first portion of the second release liner can cover the second half of the adhesive sheet 120 to inhibit the adhesive sheet 120 prematurely or inadvertently adhering to an object prior to application of the user interface 116 to the user. The second portion can have a first end that is coupled to the first portion at an inner portion of the user interface 116 (e.g., at the aperture 754), and a second end that is separate from the first portion at an outer portion of the user interface 116 (e.g., at the peripheral edge of the user interface 116). In this arrangement, a practitioner can grasp the second end at the periphery of the user interface 116 and pull outwardly away from the user to separate the first portion of the second release liner from the adhesive sheet 120. In this way, the second release liner can be progressively expose the second half the adhesive sheet 120 in a direction from the aperture 754 towards the peripheral edge of the user interface 116. This can help to improve the coupling the adhesive sheet 120 to the buttocks of the user with the aperture 754 aligned with the anus of the user.

As shown in FIG. 8B, the first half and the second half of the adhesive sheet 120 can each include a grip region 864. The grip region 864 can be located at the outer periphery of the adhesive sheet 120 and omit the adhesive. This can allow a practitioner to hold the grip region 864 to manipulate and handle the adhesive sheet 120 while applying the adhesive sheet 120 to the user's buttocks. The grip region 864 can also facilitate easier removal of the adhesive sheet 120 from the user as compared to an alternative implementation in which the adhesive extends over an entire surface area of the adhesive sheet 120.

Additionally, as shown in FIG. 8B, the user interface 116 and/or the applicator 118 can include an alignment indicator 866 that can help to align the aperture 754 and the drainage conduit 112 with the anus of the user. For example, in FIG. 8B, the alignment indicator 866 includes a first line that extends on the applicator 118 from a top of the aperture 754 to the peripheral edge of the adhesive sheet 120, and a second line that extends on the applicator 118 from a bottom of the aperture 754 to the peripheral edge of the adhesive sheet 120. In this arrangement, the alignment indicator 866 can provide a visual indication of the location of the aperture 754 of the applicator 118, the aperture 646 of the user interface 116 (shown in FIG. 6), and the drainage conduit 112 positioned between the buttocks even though the aperture 754 and the aperture 646 cannot be directly visualized.

Figure 9A:
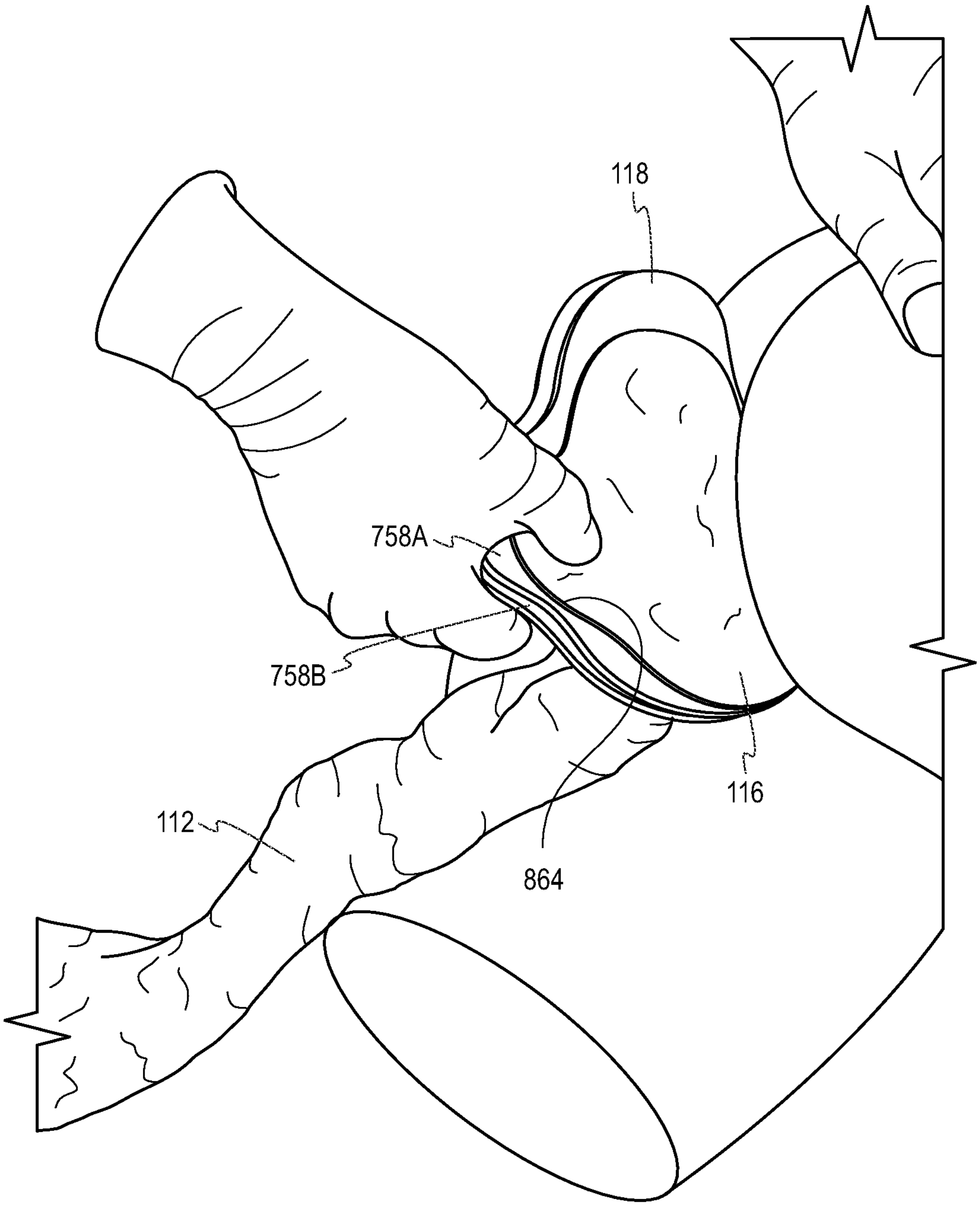
FIGS. 9A-9J illustrate a process for coupling the fecal collection system of FIG. 6 to a user, according to an example.

Referring now to FIGS. 9A-9J, process for coupling the fecal collection system 600 to a user is depicted according to one example implementation of the user interface assembly 110. In FIG. 9A, the user interface assembly 110 is inserted between the buttocks of the user. For instance, with the applicator 118 in the folded state, a medical practitioner can hold the first tab 758A and the second tab 758B of the applicator 118 along with the grip regions 864 of the adhesive sheet 120. As shown in FIG. 9A, this allows the medical practitioner to hold the user interface assembly 110 at a location remote from the buttocks while positioning the aperture in the user interface 116 and the drainage conduit 112 at the anus.

Figure 9B:
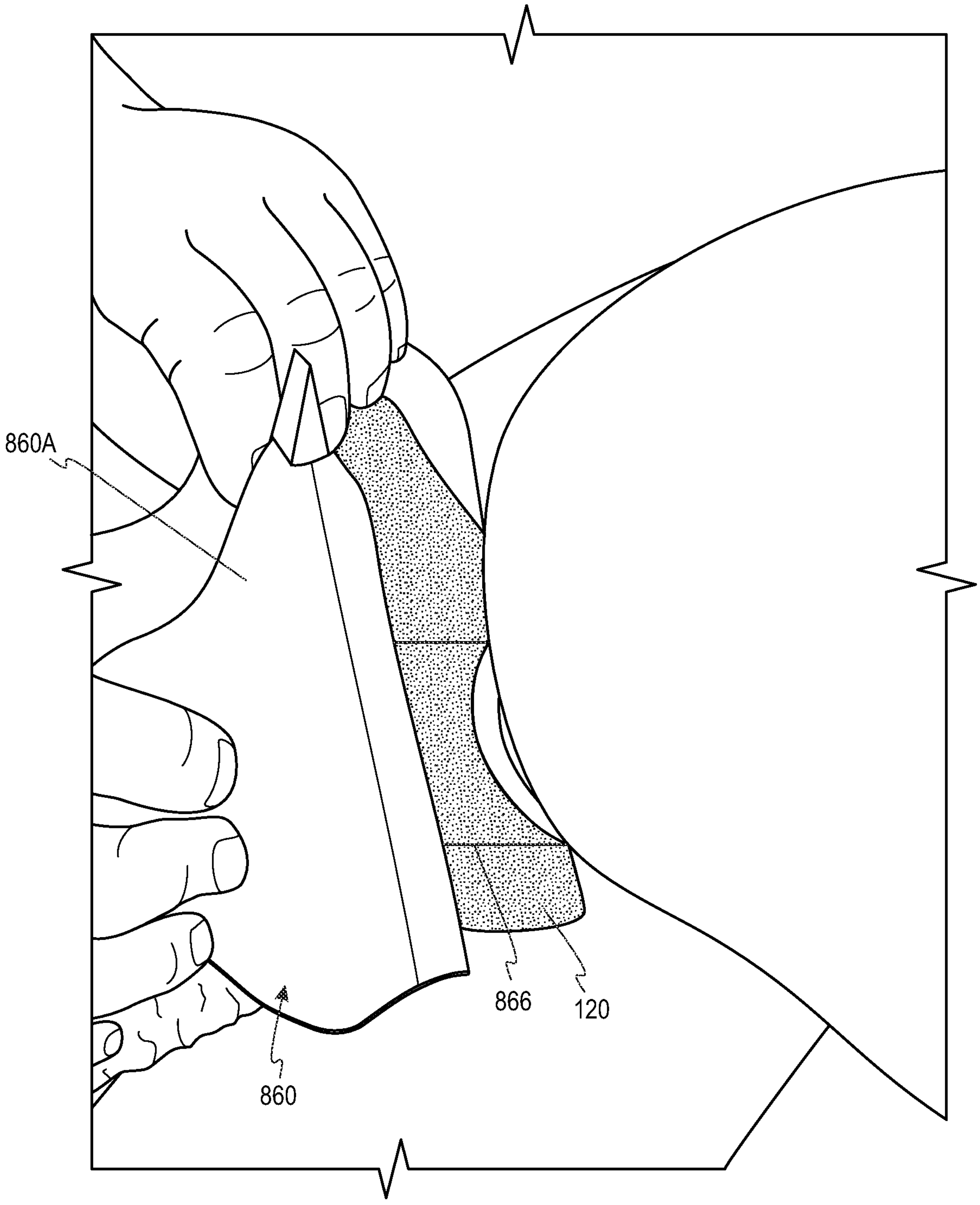

In FIG. 9B, the first release liner 860 is removed from the first half of the adhesive sheet 120. For example, the medical practioner can grasp the second end at the periphery of the user interface 116 and pull outwardly away from the user to separate the first portion 860A of the first release liner 860 from the adhesive sheet 120. In this way, the first release liner 860 can be progressively expose the first half the adhesive sheet 120 in a direction from the aperture 754 towards the peripheral edge of the user interface 116.

Figure 9C:
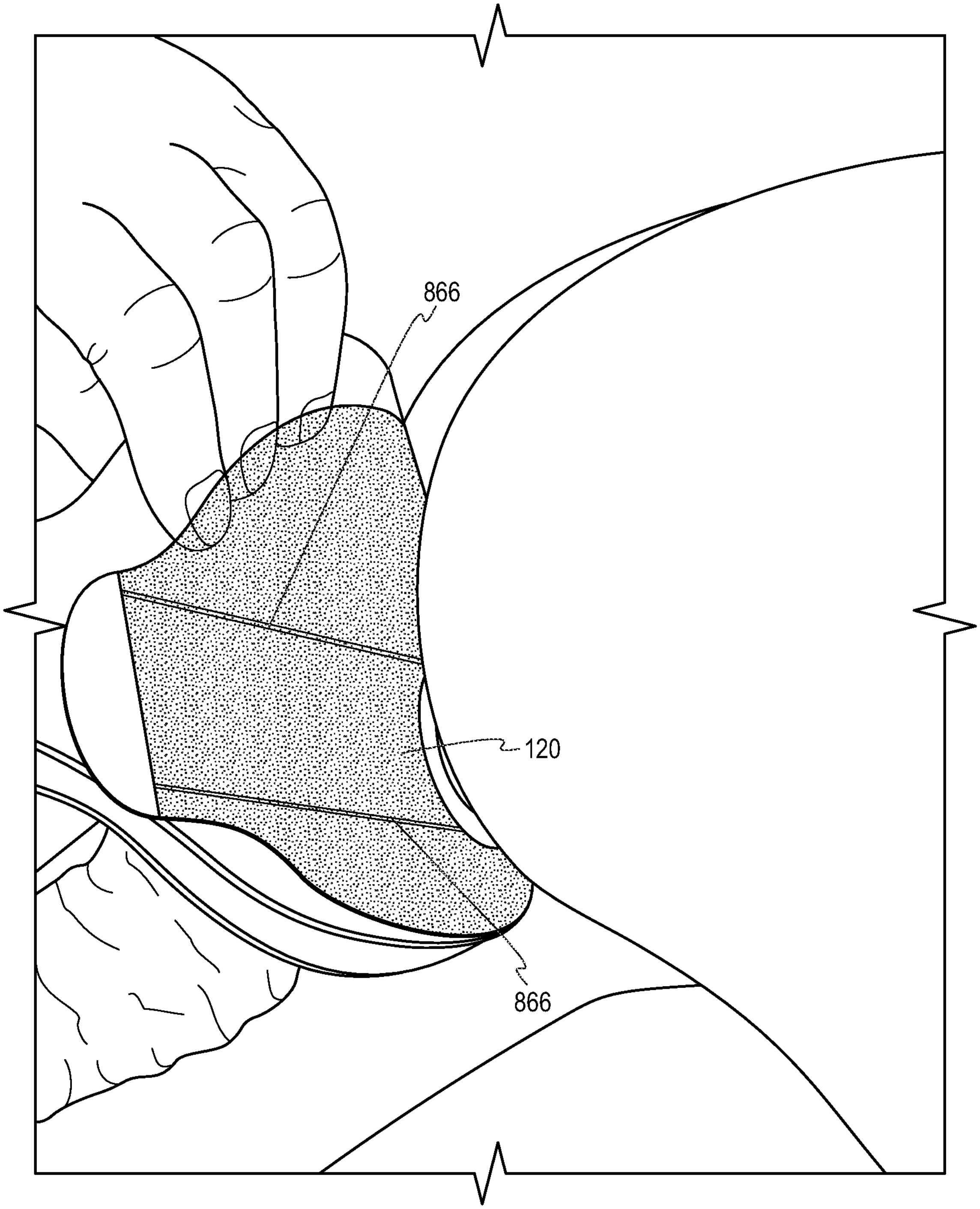

In FIG. 9C, after the first release liner 860 is removed from the adhesive sheet 120, the medical practitioner can use the alignment indicator 866 to determine the position of the aperture relative to the anus of the user. In some instance, the medical practitioner can use the applicator 118 to adjust a position of the user interface 116 relative to the user based on a position of the alignment indicator relative to the anus of the user.

Figure 9D:
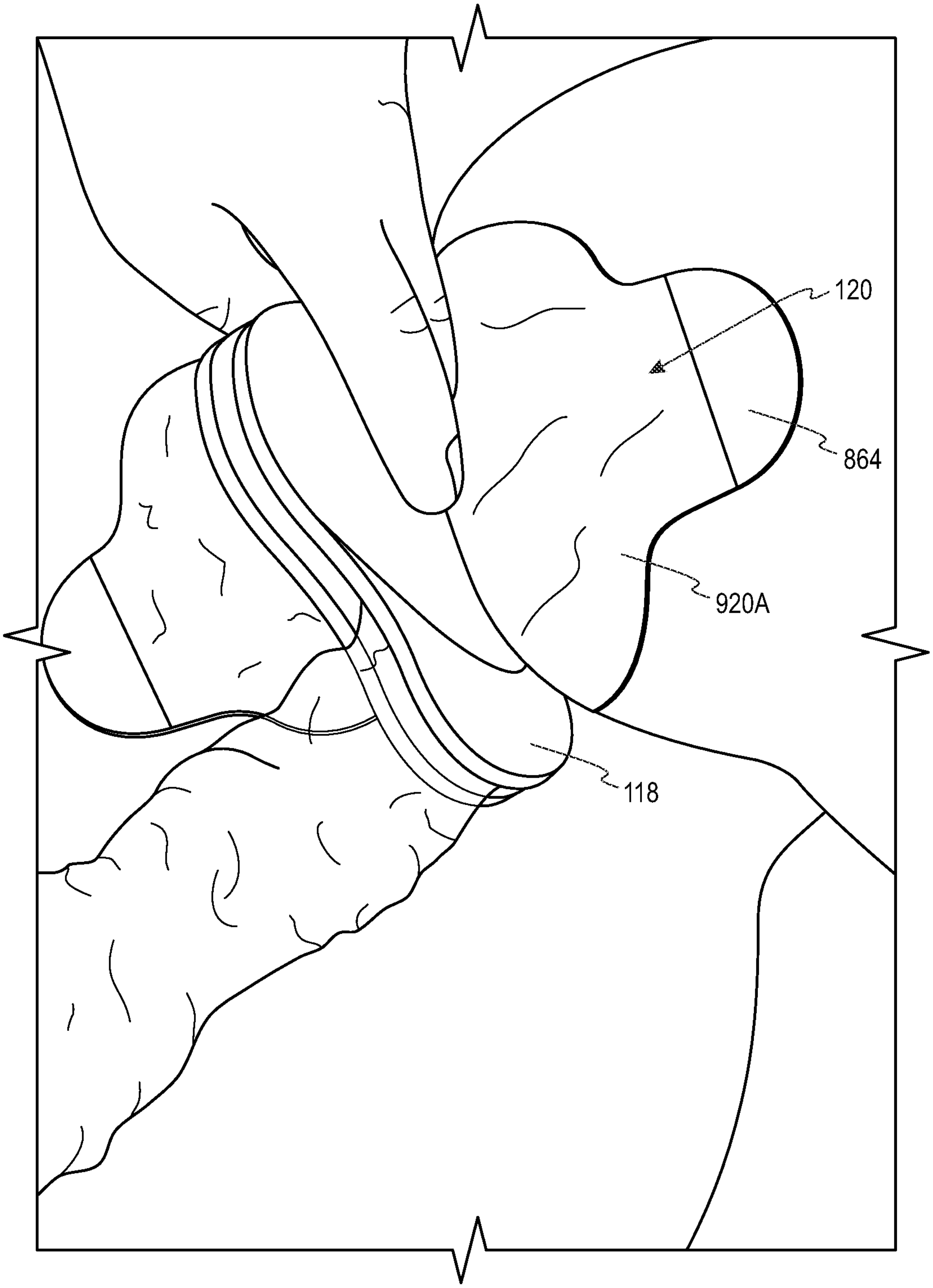

In FIG. 9D, the first half 920A of the adhesive sheet 120 can be coupled to the skin of the user on a first buttock. Additionally, as shown in FIG. 9D, the medical practioner can use one hand to hold the applicator 118 in position at the anus while using the other hand to place the first half 920A of the adhesive sheet 120 on the first buttock (e.g., by holding the grip region 864 of the adhesive sheet 120).

Figure 9E:
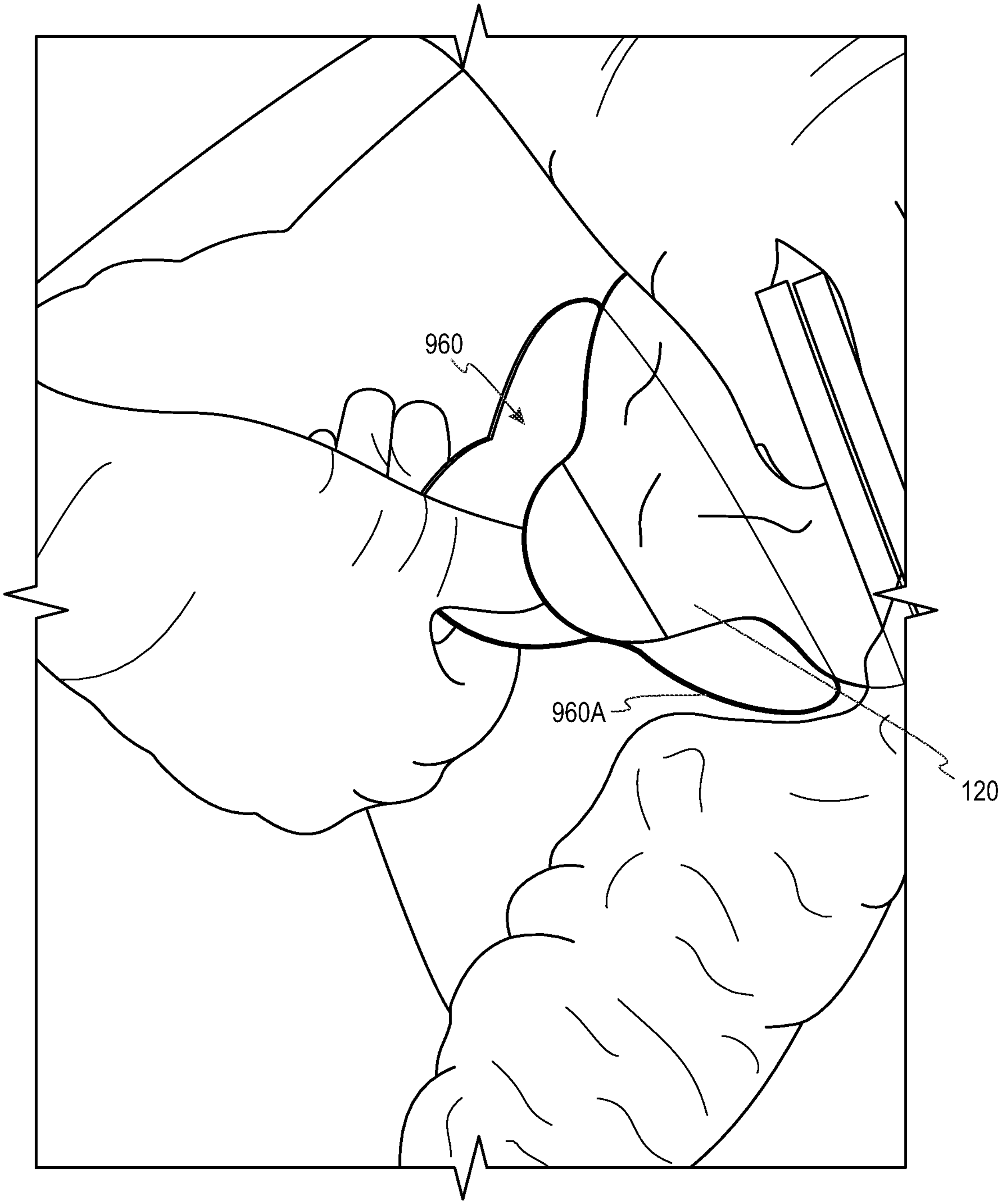

In FIG. 9E, the second release liner 960 is removed from the second half of the adhesive sheet 120. For example, the medical practioner can grasp the second end at the periphery of the user interface 116 and pull outwardly away from the user to separate the first portion 960A of the second release liner 960 from the adhesive sheet 120. In this way, the second release liner 960 can be progressively expose the second half the adhesive sheet 120 in a direction from the aperture 754 towards the peripheral edge of the user interface 116.

Figure 9F:
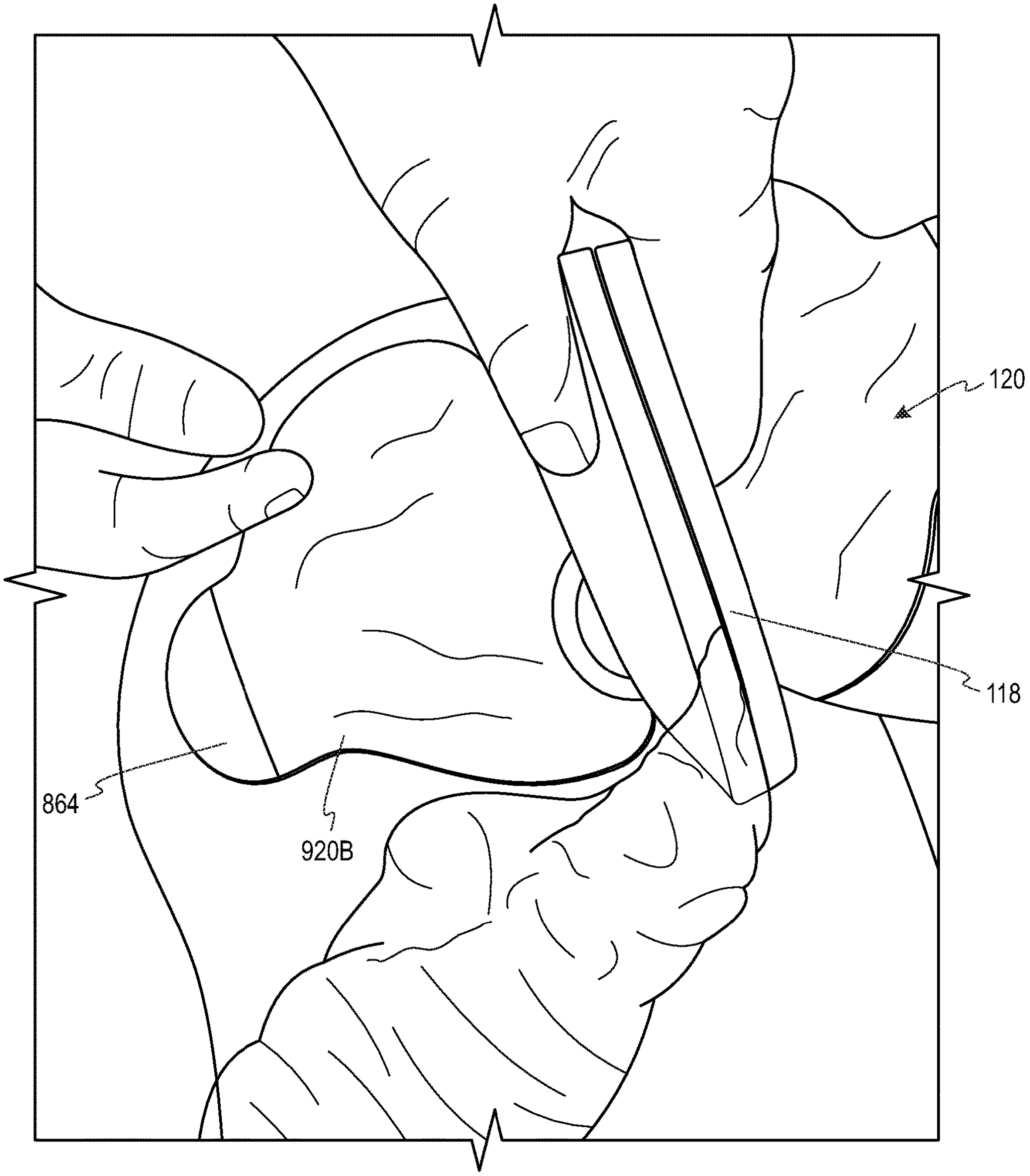

In FIG. 9F, the second half 920B of the adhesive sheet 120 can be coupled to the skin of the user on a second buttock. Additionally, as shown in FIG. 9F, the medical practioner can use one hand to hold the applicator 118 in position at the anus while using the other hand to place the second half 920B of the adhesive sheet 120 on the second buttock (e.g., by holding the grip region 864 of the adhesive sheet 120).

Figure 9G:
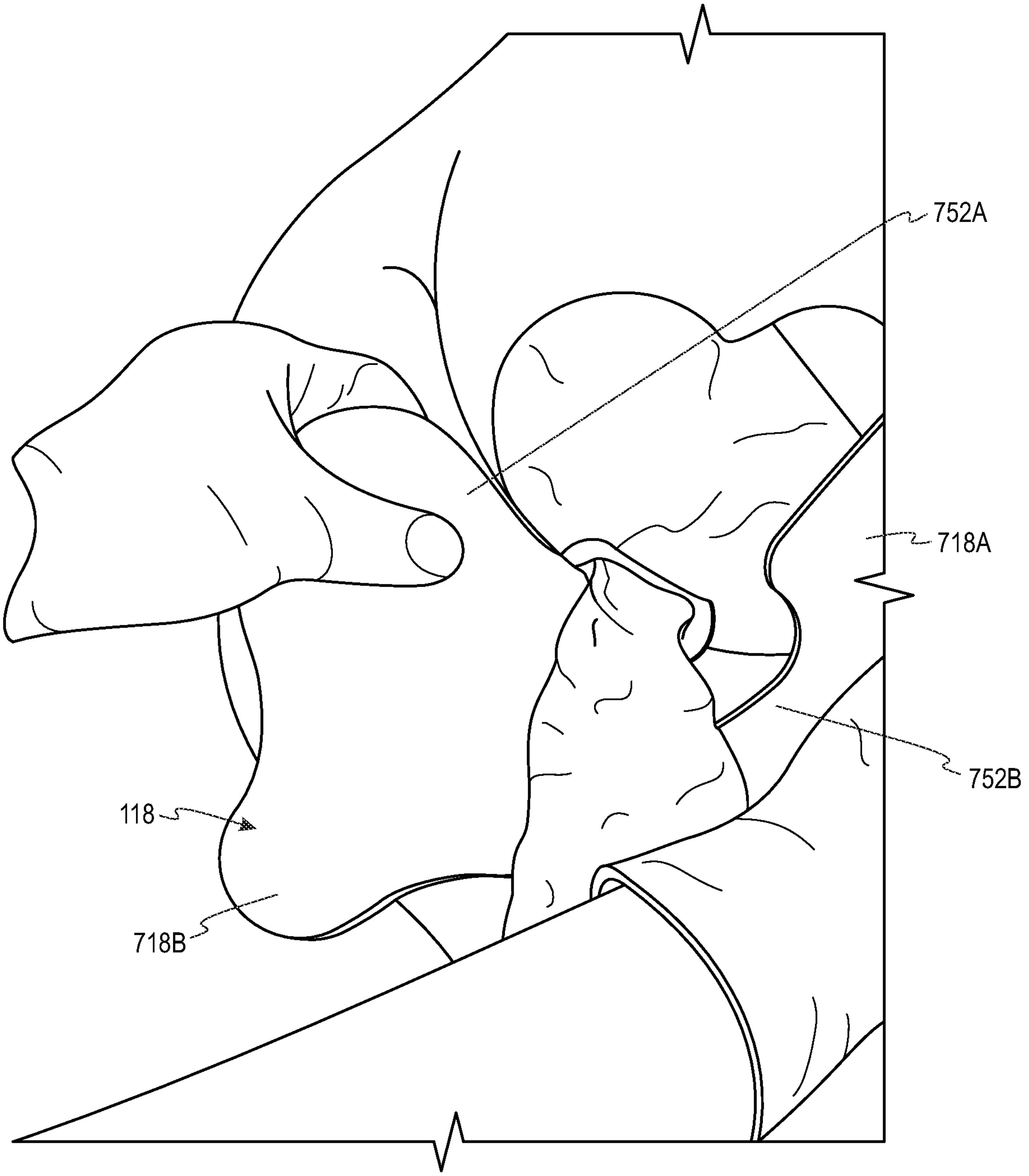
Figure 9H:
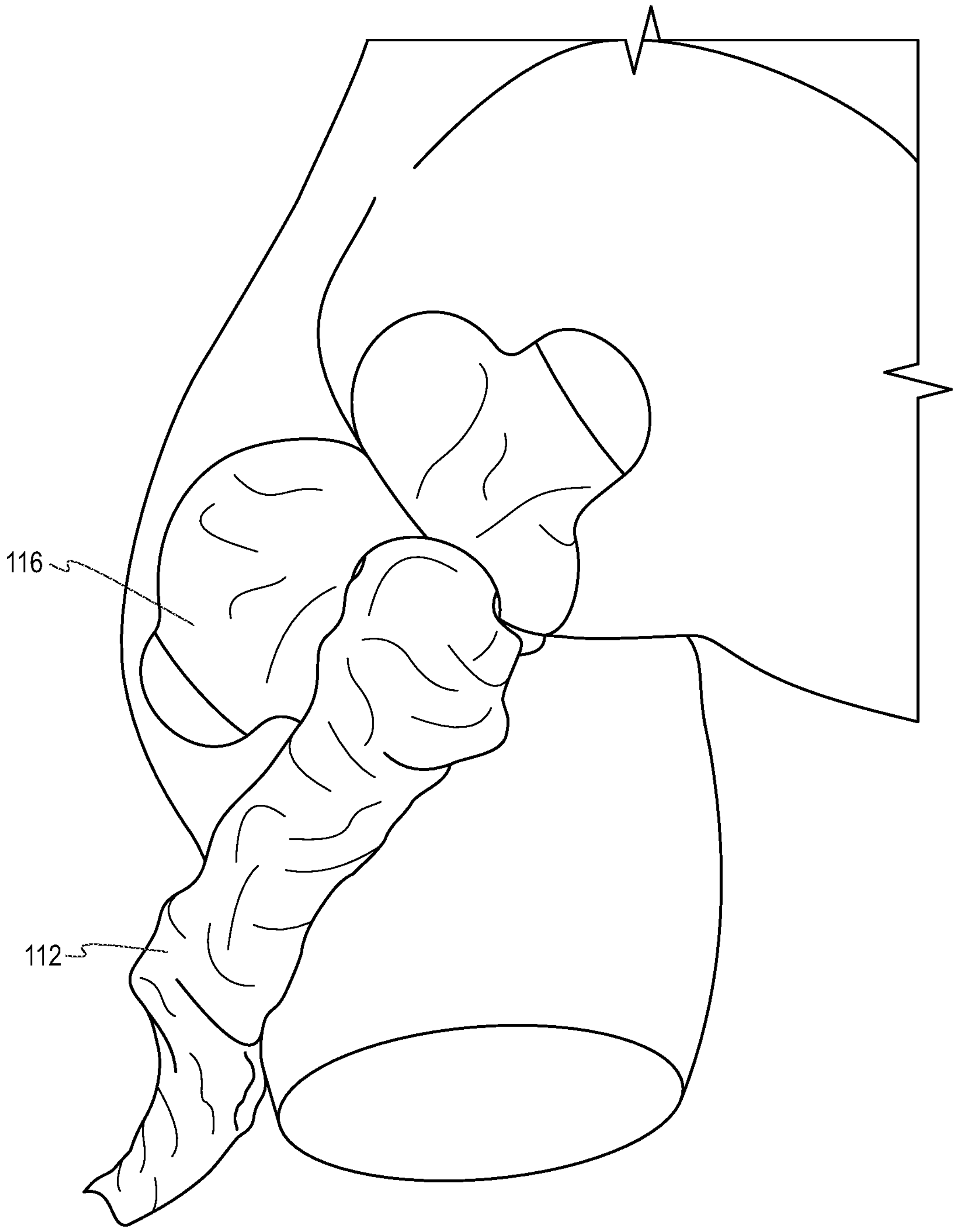
Figure 9I:
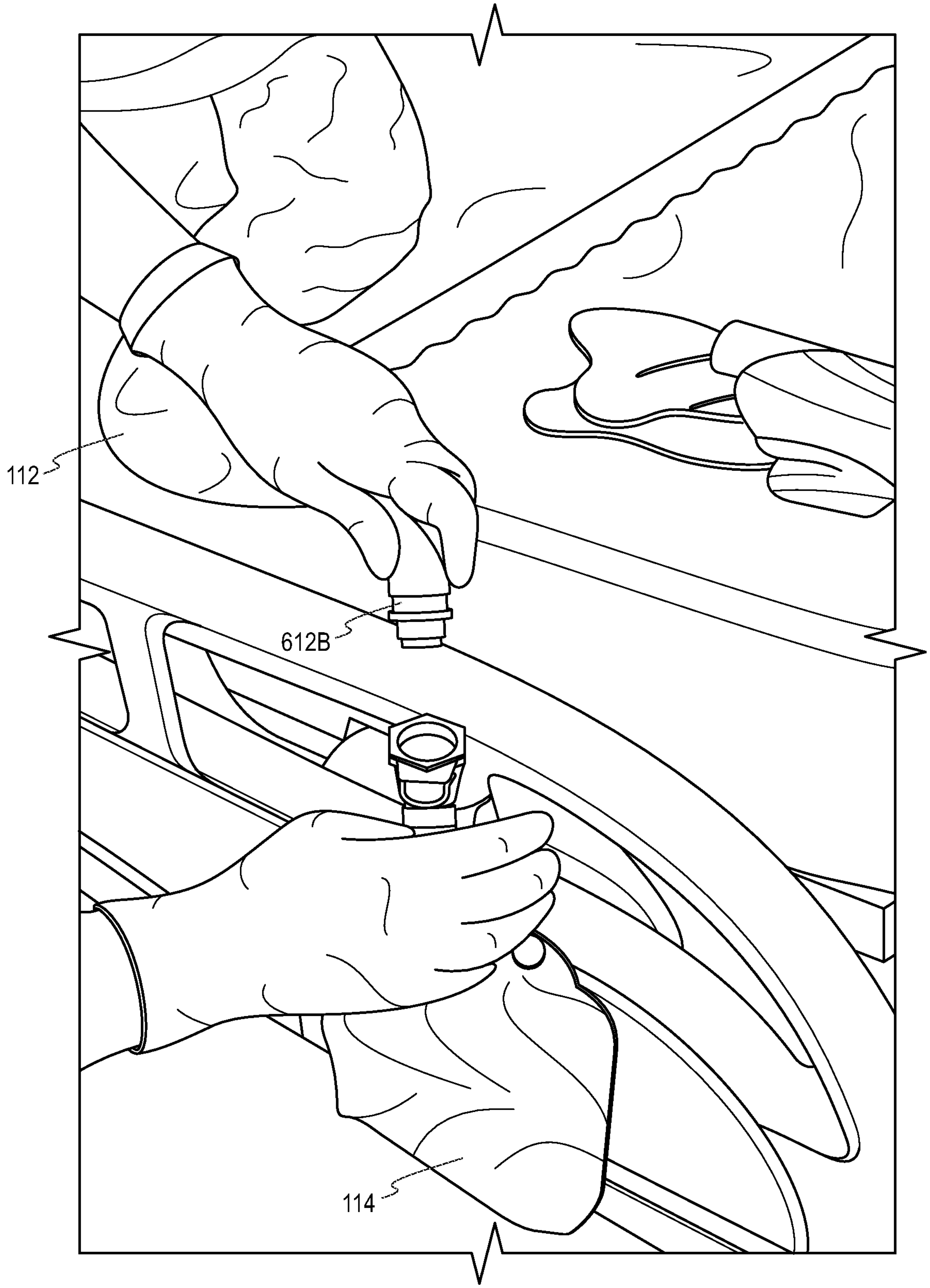
Figure 9J:
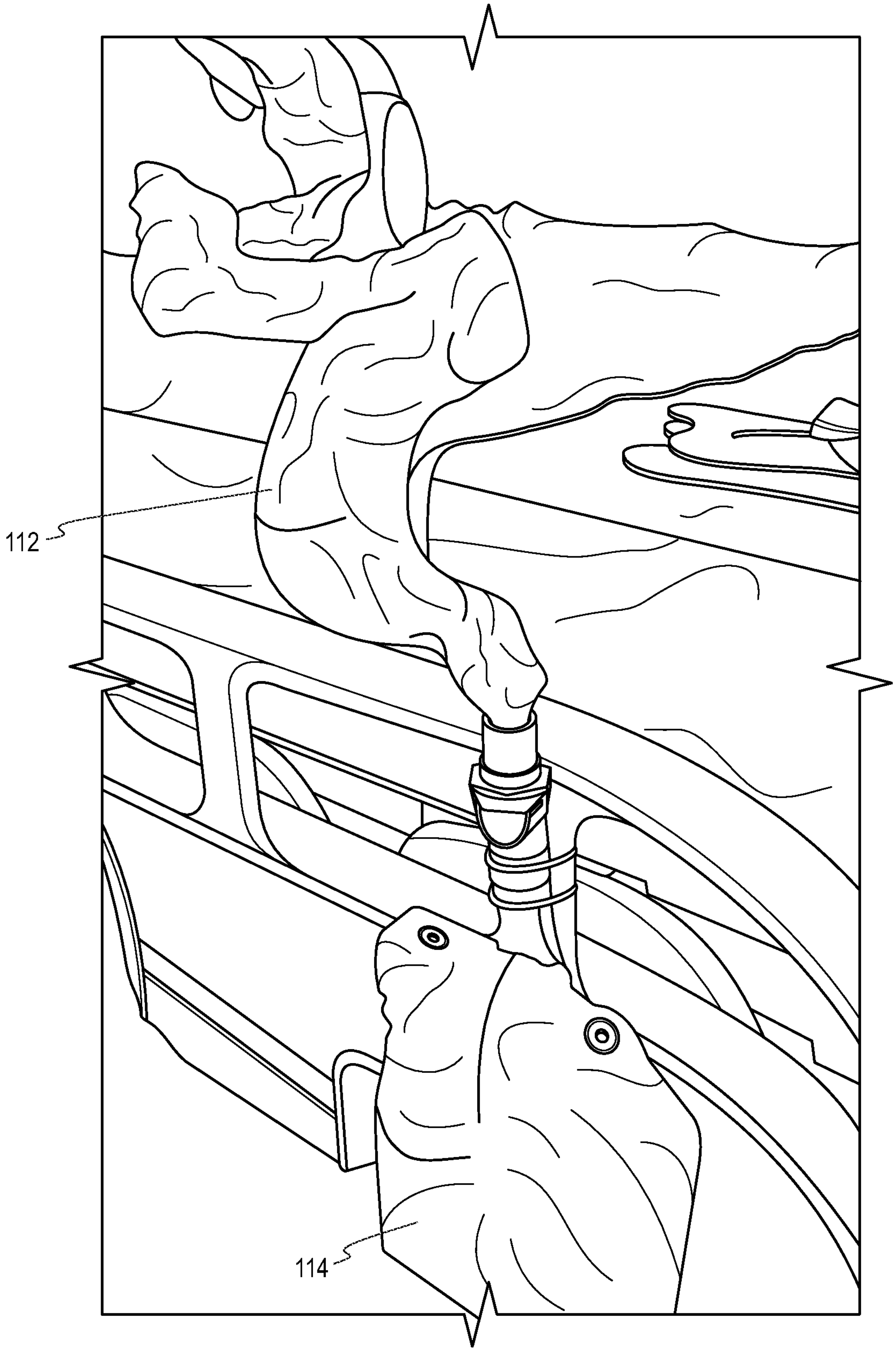

FIG. 9G depicts the applicator 118 being removed from the user interface 116 and FIG. 9H depicts the user interface 116 and the drainage conduit 112 after the applicator 118 has been removed from the user interface 116. For example, as shown in FIG. 9G, the first lateral portion 718A and the second lateral portion 718B can be torn apart from each other (e.g., at the first bridge portion 752A and/or the second bridge portion 752B). This can facilitate completely removing the applicator 118, which can help to improve user comfort and reduce pressure on the user's buttocks. However, in another example, the applicator 118 can be decoupled from the remainder of the user interface 116 (e.g., the adhesive sheet 120 and the collar 122, and then moved distally along the drainage conduit 112 away from the user (e.g., with the first bridge portion 752A and the second bridge portion 752B intact). FIGS. 9I-9J depicts the distal end 612B of the drainage conduit 112 being coupled to the collection reservoir 114. As shown in FIGS. 9I-9J, the collection reservoir 114 can be coupled to the side of a patient support structure (e.g., a hospital bed).

Although the applicator 118 includes the first lateral portion 318A, 618A and the second lateral portion 318B, 618B in FIGS. 3A-9J, the applicator 118 can have a different configuration in other examples. FIGS. 10A-13B depict aspects of the user interface 116 and/or the applicator 118 according to some other examples.

Figure 10A:
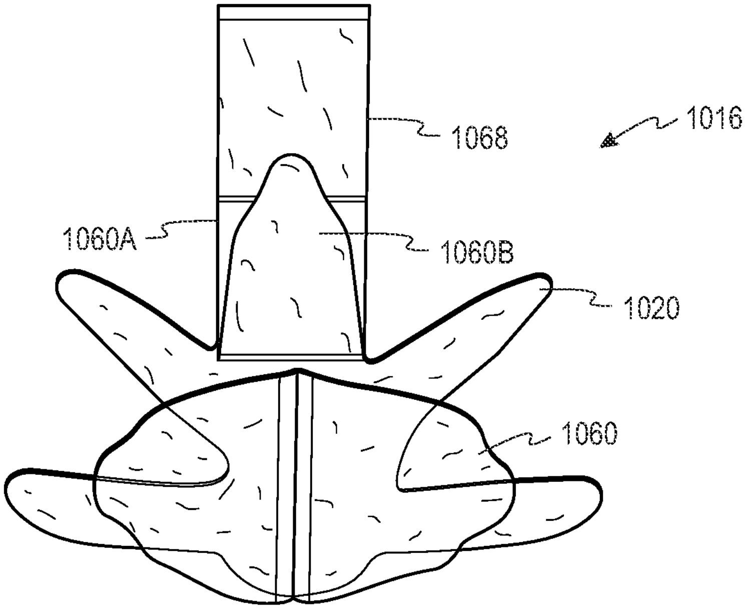
FIG. 10A illustrates a distal side of a user interface, according to an example.
Figure 10B:
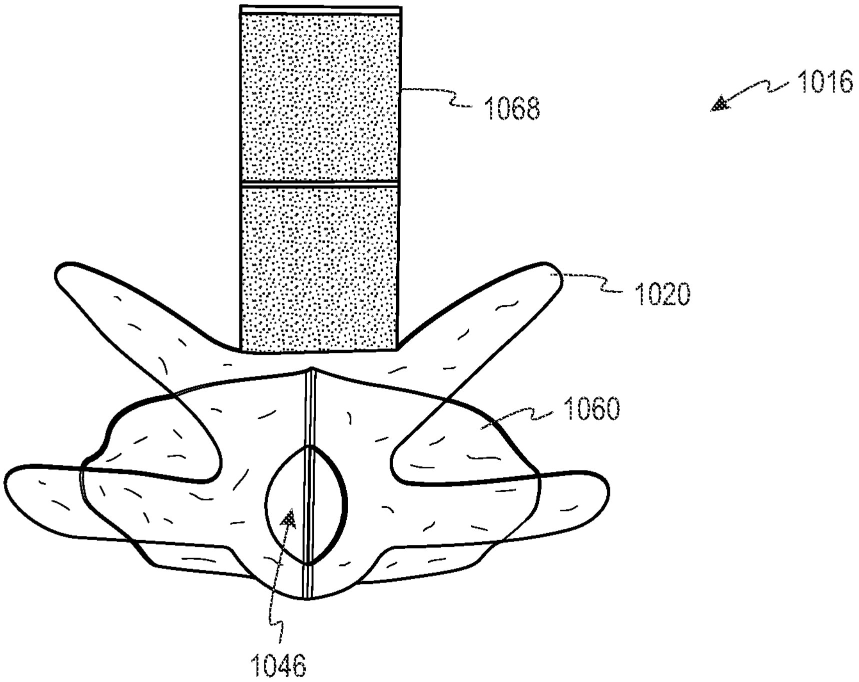
FIG. 10B illustrates a proximal side of the user interface shown in FIG. 10A, according to an example.

FIGS. 10A-10B depict a user interface 1016 for an implementation of the user interface 116 according to another example. As shown in FIG. 10A-10B, the user interface 1016 can include an adhesive sheet 1020, a release liner 1060, and an aperture 1046 in the adhesive sheet 1020. The adhesive sheet 1020 is substantially similar or identical to the adhesive sheet 120 described above, except the adhesive sheet 1020 in FIGS. 10A-10B can have a different shape. For example, in FIGS. 10A-10B, the adhesive sheet 1020 can include a plurality of arms that extend outwardly from a central portion. The central portion of the adhesive sheet 1020 can define the aperture 1046.

Additionally, the user interface 1016 includes a sacral pressure pad 1068. The sacral pressure pad 1068 can extend from a top edge of the adhesive sheet 1020 such that the sacral pressure pad 1068 is configured to be located adjacent to a sacrum of a user when the adhesive sheet 120 is coupled to the skin of the user with the aperture 1046 aligned with the anus of the user. The sacral pressure pad 1068 can have a thickness and a pliability that assists in reducing a pressure on the sacrum when the sacral pressure pad 1068 is positioned between the sacrum of the user and a support surface (e.g., a hospital bed and/or a wheel chair).

In some examples, the sacral pressure pad 1068 can include an adhesive that that is configured to couple the sacral pressure pad 1068 to the sacrum of the user. In such examples, the release liner 1060 can also include a sacral portion that covers the adhesive on the sacral pressure pad 1068 prior to adhering the sacral pressure pad 1068 to the user.

Similar to the first and second release liners described above, the sacral portion of the release liner 1060 can include a first portion 1060A and a second portion 1060B. The first portion 1060A can cover the adhesive on the sacral pressure pad 1068 to inhibit the adhesive prematurely or inadvertently adhering to an object prior to application of the user interface 116 to the user. The second portion 1060B can have a first end that is coupled to the first portion 1060A at an inner portion of the sacral pressure pad 1068 (e.g., at an end closest to the adhesive sheet 1020), and a second end that is separate from the first portion 1060A at an outer portion of the sacral pressure pad 1068 (e.g., at an end farthest away from the adhesive sheet 1020). In this arrangement, a practitioner can grasp the second end of the second portion 1060B and pull outwardly away from the user and the adhesive sheet 1020 to separate the first portion 1060A of the release liner 1060 from the adhesive on the sacral pressure pad 1068. In this way, the release liner 1060 can be progressively expose the adhesive on the sacral pressure pad 1068 in a direction from the adhesive sheet 1030 towards the peripheral edge of the user interface 116. This can help to improve coupling the adhesive to the sacrum.

Figure 11A:
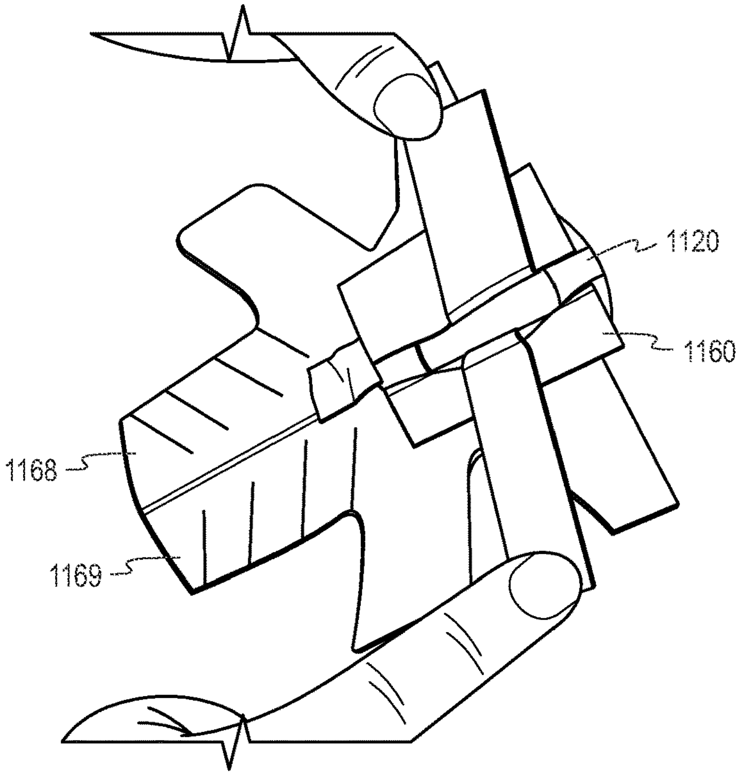
FIG. 11A depicts a user interface, according to another example.
Figure 11B:
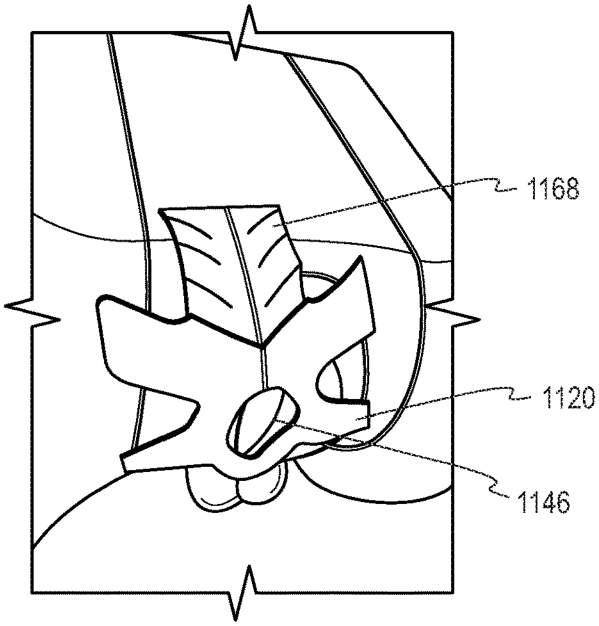
FIG. 11B depicts the user interface of FIG. 11A coupled to a user, according to an example.

FIGS. 11A-11B depict a user interface 1116 for an implementation of the user interface 116 according to another example. As shown in FIG. 11A-11B, the user interface 1116 can include an adhesive sheet 1120, a release liner 1160, an aperture 1146 in the adhesive sheet 1120, and a sacral pressure pad 1168. However, in this example, the sacral pressure pad 1168 includes a plurality of slits 1169. The slits 1169 in the sacral pressure pad 1168 can help to splay the sacral pressure pad 1168 over the sacrum of the user, and can assist in removing the sacral pressure pad 1168 from the user. These functions can be further enhanced by arranging the slits 1169 at a diagonal orientation relative to a longitudinal axis of the sacral pressure pad 1168.

Figure 12A:
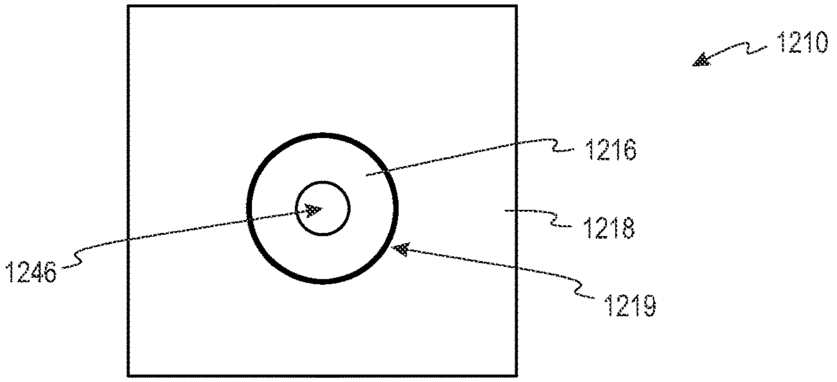
FIG. 12A depicts a user interface assembly in a first configuration, according to another example.
Figure 12B:
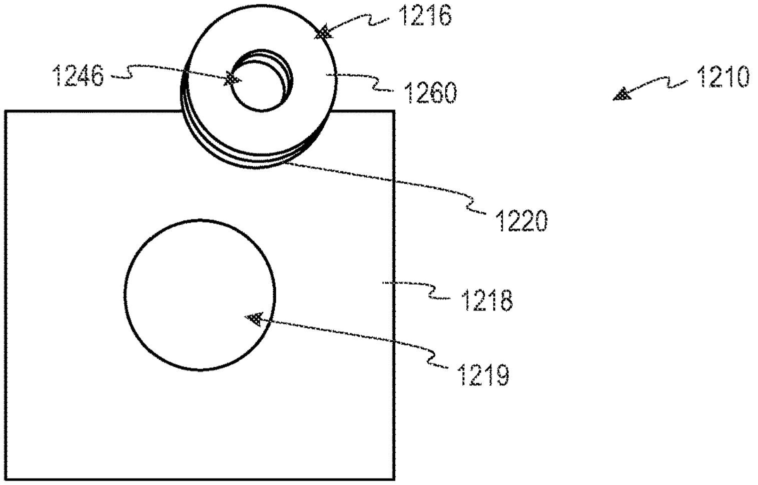
FIG. 12B depicts the user interface assembly of FIG. 12A in a second configuration, according to an example.
Figure 12C:
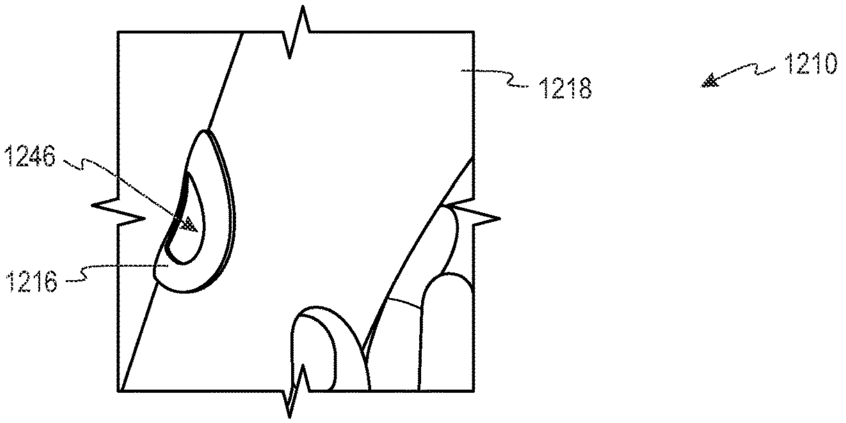
FIG. 12C depicts the user interface assembly of FIG. 12A in the first configuration while the user interface assembly is being applied to a user, according to an example.

FIGS. 12A-12C depict a user interface assembly 1210 including a user interface 1216 and an applicator 1218 for an implementation of the user interface 116 and the applicator 118 and according to another example. In FIGS. 12A-12C, the user interface 1216 is disposed within an aperture 1219 in the applicator 1218 while coupling the user interface 1216 to the user, and the applicator 1218 and the user interface 1216 are configured to decouple from each other after coupling the user interface 1216 to the user.

In this example, the user interface 1216 defines an aperture 1246 that is configured to communicate with the lumen of the drainage tube 112 described above. AS shown in FIG. 12B, the user interface 1216 can also include an adhesive sheet 1220 and a release liner 1260, as described above.

FIG. 12A and FIG. 12C depict the user interface assembly 1210 in a first configuration in which the user interface 1216 is received in the aperture 1219 of the applicator 1218. As shown in FIG. 12C, the user interface assembly 1210 is configured to be bent and/or folded along an axis extending through the user interface 1216 without the user interface 1216 decoupling from the applicator 1218. In this first configuration, an operator can hold the applicator 1218 while coupling the user interface 1216 to the user in a manner similar to that described above.

FIG. 12B depicts the user interface assembly 1210 in a second configuration in which the user interface 1216 is decoupled from the applicator 1218. In an example, the adhesive 1220 can have a first breakaway force that defines an amount of force that is required to remove the user interface 1216 from the skin of the user, and the user interface assembly 1210 can have a second breakaway force that defines an amount of force that is required to decouple the applicator 1218 from the user interface 1216 along an interface between the applicator 1218 and the user interface 1216 (e.g., along a circumference of the aperture 1219). The first breakaway force can be greater than the second breakaway force. In this arrangement, when the user interface 1216 is coupled to the skin of the user, the operator can decouple and remove the applicator 1218 by pulling the applicator 1218 away from the user interface 1216 with a force that is (i) greater than the second breakaway force and (ii) less than the first breakaway force.

Figure 13A:
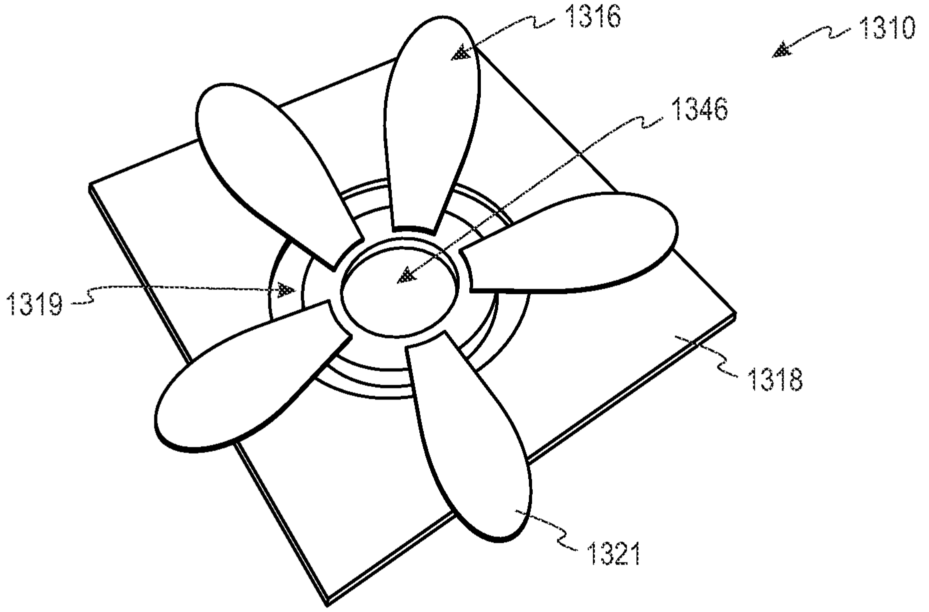
FIG. 13A depicts a user interface assembly in a first configuration, according to another example.
Figure 13B:
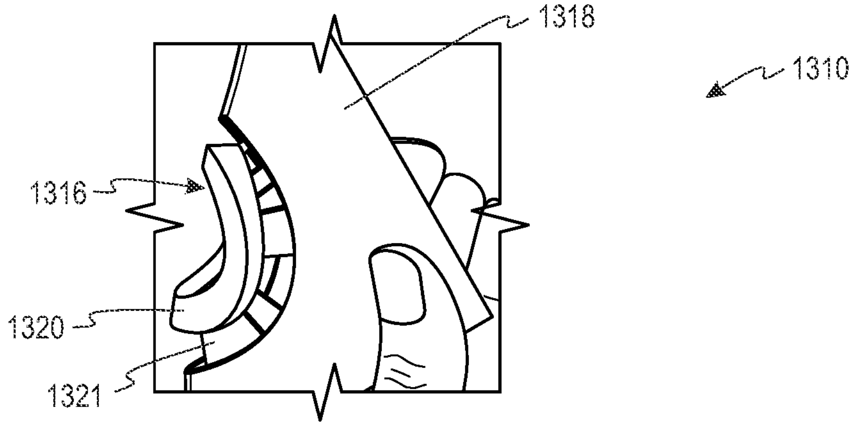
FIG. 13B depicts the user interface assembly of FIG. 13A in the first configuration while the user interface assembly is being applied to a user, according to an example.
Figure 14:
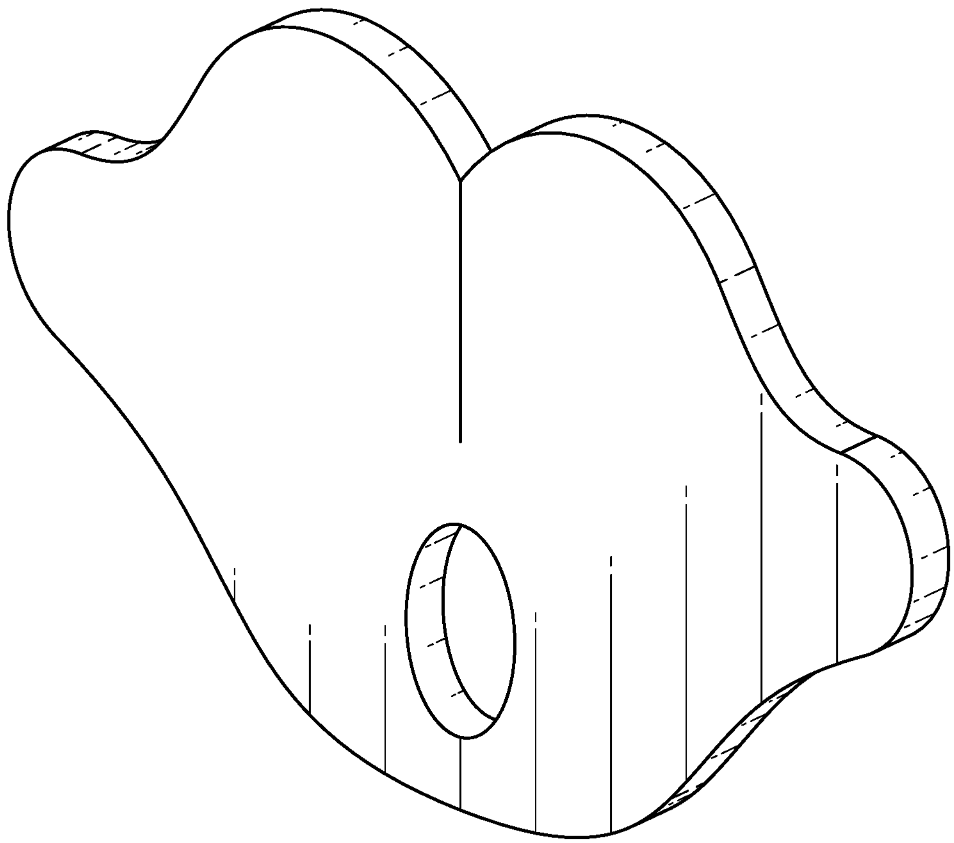
FIG. 14 is a perspective view of an applicator, according to an example.
Figure 15:
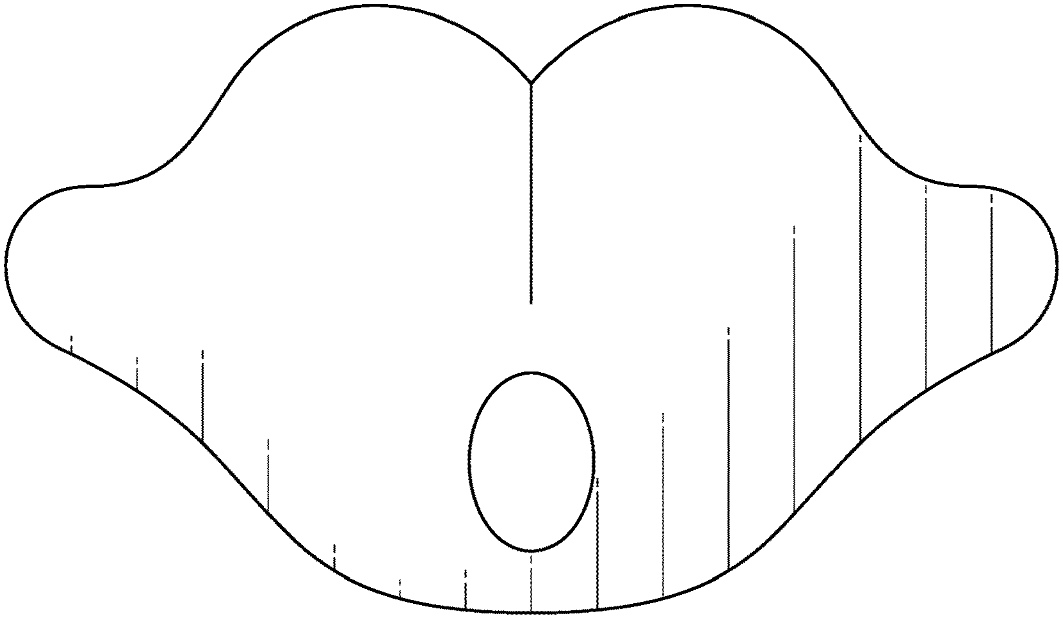
FIG. 15 is a first side view of the applicator shown in FIG. 14, according to the example.
Figure 16:
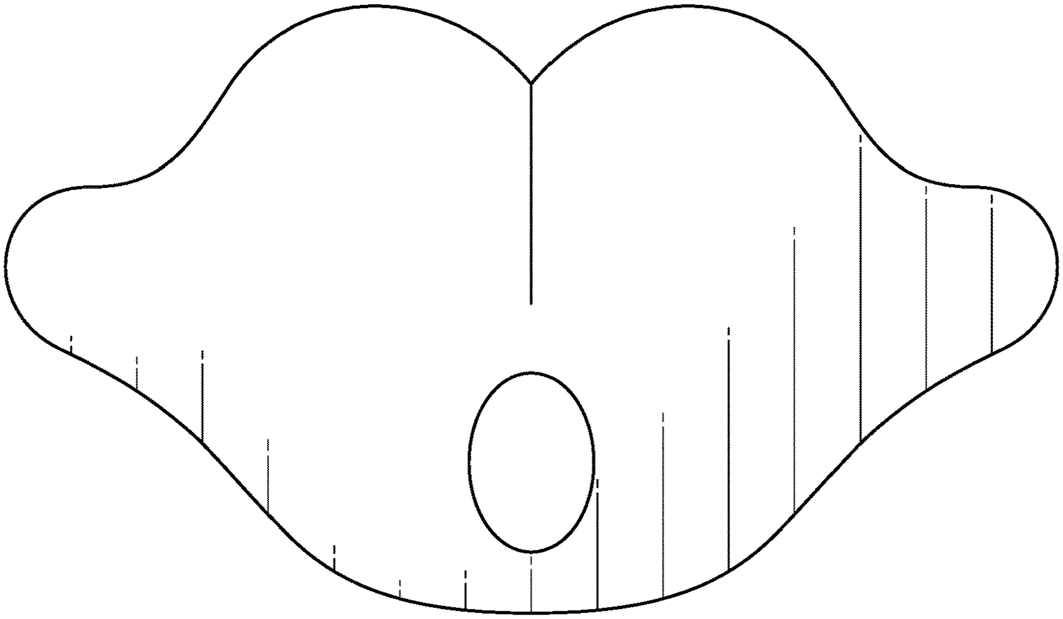
FIG. 16 is a second side view of the applicator shown in FIG. 14, according to the example.
Figure 17:
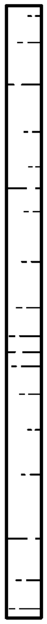
FIG. 17 is a first side view of the applicator shown in FIG. 14, according to the example.
Figure 18:
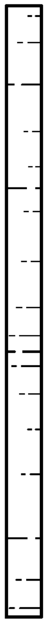
FIG. 18 is a second side view of the applicator shown in FIG. 14, according to the example.
Figure 19:
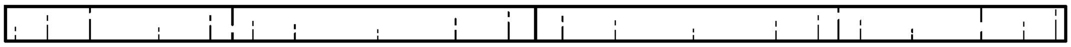
FIG. 19 is a first side view of the applicator shown in FIG. 14, according to the example.
Figure 20:
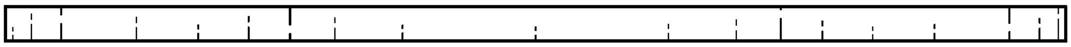
FIG. 20 is a second side view of the applicator shown in FIG. 14, according to the example.

FIGS. 13A-13B depict a user interface assembly 1310 including a user interface 1316 and an applicator 1318 for an implementation of the user interface 116 and the applicator 118 and according to another example. The user interface assembly 1310 is substantially similar to the user interface assembly 1210 of FIGS. 12A-12C, except the user interface assembly 1310 includes a user interface 1316 having a plurality of arms extending from a central ring, which defines an aperture 1346 for communicating with the lumen of the drainage conduit 112.

Similar to the user interface assembly 1210 of FIGS. 12A-12C, the user interface 1316 is disposed within an aperture 1319 in the applicator 1318 while coupling the user interface 1316 to the user, and the applicator 1318 and the user interface 1316 are configured to decouple from each other after coupling the user interface 1316 to the user. However, the user interface assembly 1310 of FIGS. 13A-13B differs from the user interface assembly 1210 in that the arms of the user interface 1316 extend beyond the aperture 1346 and are coupled to the distal side of the applicator 1318 when in the first configuration. After coupling an adhesive sheet 1320 on the central ring of the user interface 1316 to the skin of a user, the applicator 1318 can be pulled away from the user interface 1316 with a force between the first breakaway force and the second breakaway force described above to decouple the applicator 1318 from the user interface 1316. In this example, while decoupling the applicator 1318 from the user interface 1316, the arms can pass through the aperture 1319 of the applicator 1318.

FIGS. 14-20 depict additional views of the applicator 118 shown in FIGS. 6-9G according to an example.

Figure 21:
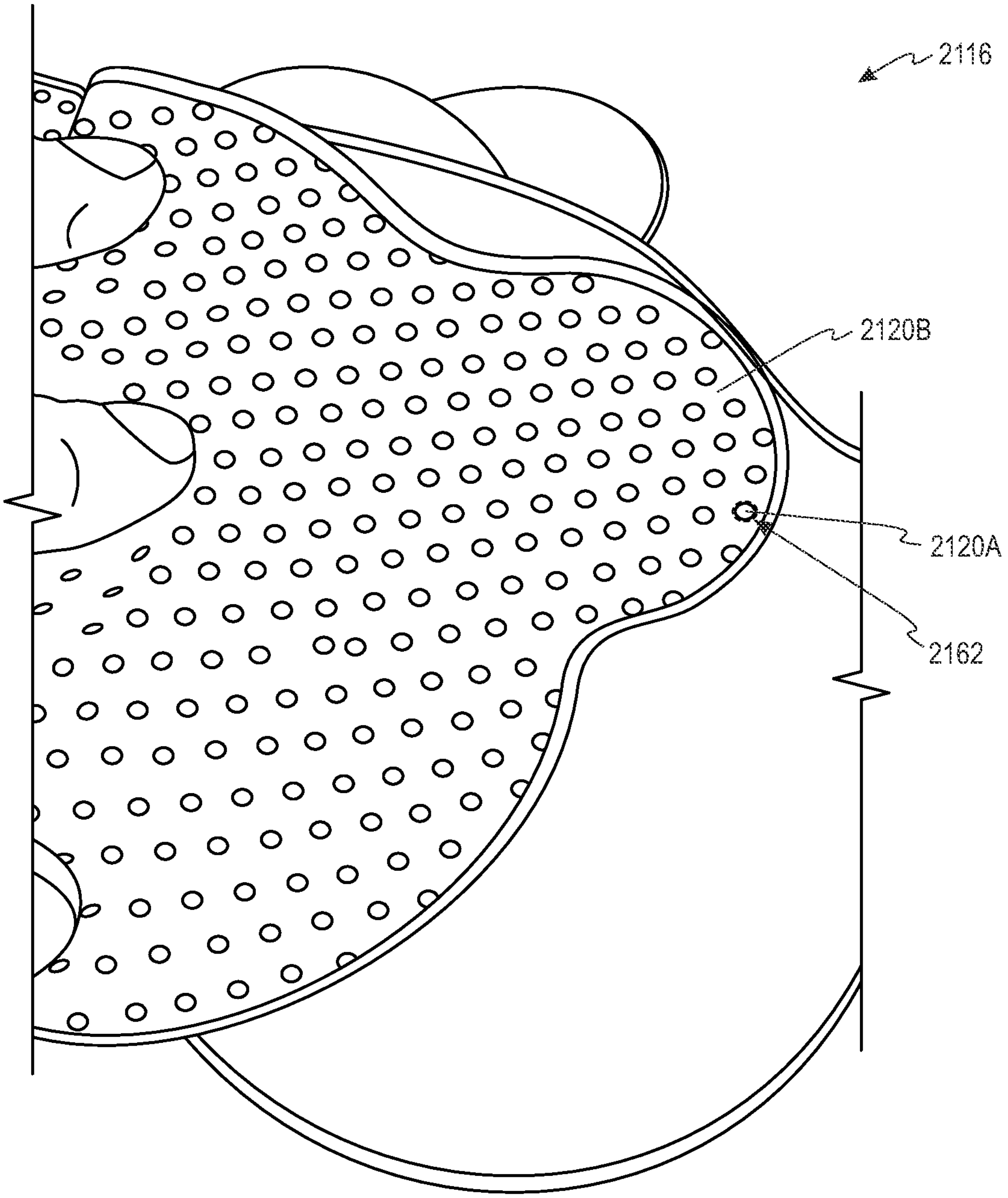
FIG. 21 depicts a user interface, according to another example.

FIG. 21 depicts a user interface 2116 according to another example. The user interface 2116 shown in FIG. 21 is substantially similar or identical to the user interface 116 described above, except the user interface 2116 includes a plurality of adhesive sheets 2120A, 2021B. In particular, the adhesive sheets can include a first adhesive sheet 2120A and a second adhesive sheet 2120B. The first adhesive sheet 2120A is coupled to the proximal side of the user interface 2116, and the second adhesive sheet 2120B is coupled to a proximal side of the first adhesive sheet 21020B. As shown in FIG. 21, the second adhesive sheet 2120B includes a plurality of apertures 2162. In this arrangement, the first adhesive sheet 2120A is located between the second adhesive sheet 2120B and the user interface 2116, and portions of the first adhesive sheet 2120A are exposed through the apertures 2162 in the second adhesive sheet 2120B.

As shown in FIG. 21, the apertures can be distributed over an entirety of the second adhesive sheet 2120B. However, in other examples, a portion of the second adhesive sheet 2120*b* can omit the apertures. In some examples, the apertures can be uniformly distributed over one or more portions (or an entirety) of the second adhesive sheet 2120B. Although the apertures 2162 are circular in FIG. 21, the apertures 2162 can have a different shape in other examples (e.g., hexagonal shape, other polygonal shapes, and/or non-polygonal shapes).

The first adhesive sheet 2120A has a first adhesive strength, and the second adhesive sheet 2120B has a second adhesive strength, which is different than the first adhesive strength. This can help to control the overall adhesive strength applied to the skin. In one example, the first adhesive strength is greater than the second adhesive strength. In another example, the first adhesive strength is less than the second adhesive strength.

Figure 22A:
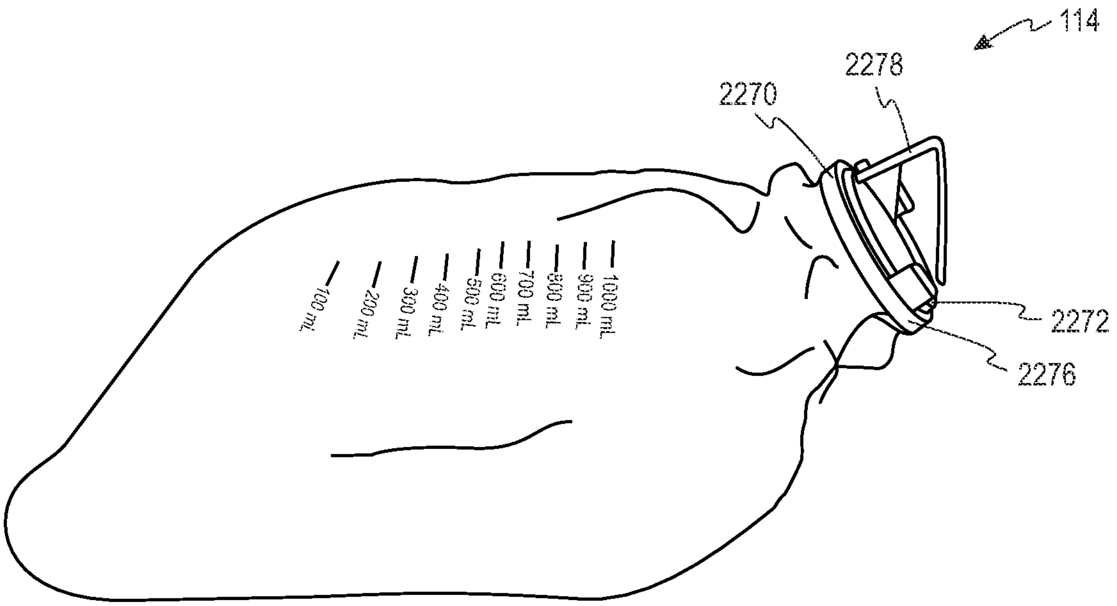
FIG. 22A depicts a collection reservoir with a cap in a closed state according to an example.
Figure 22B:
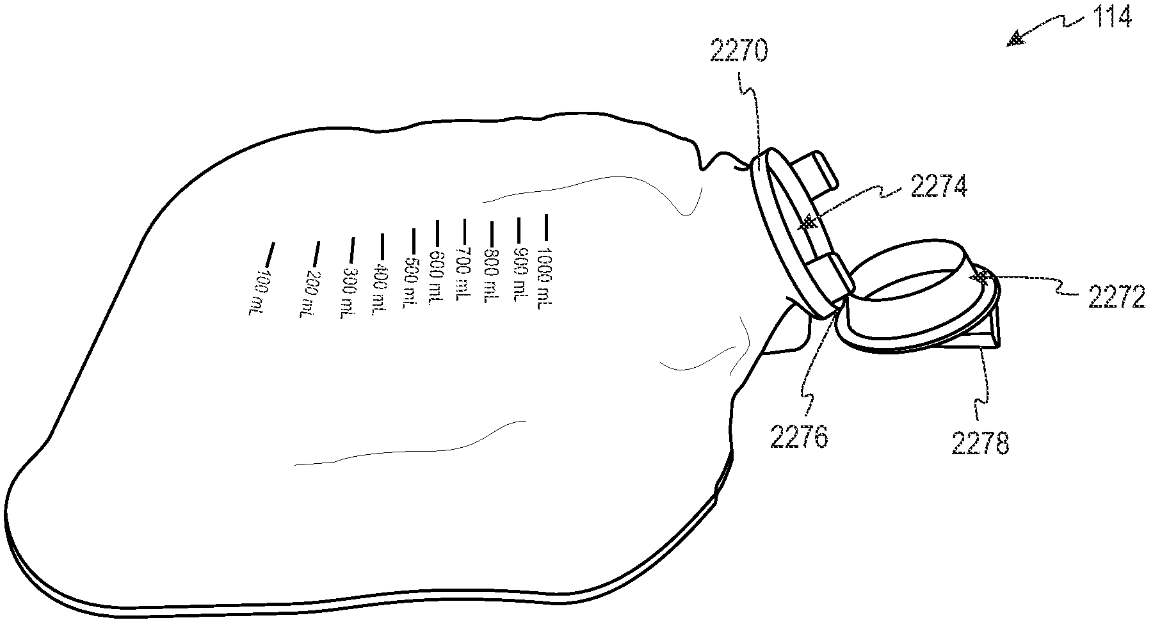
FIG. 22B depicts the collection reservoir of FIG. 22A with the cap in an open state according to an example.

Referring now to FIGS. 22A-22B, an implementation of the collection reservoir 114 according to another example. As described above, the collection reservoir 114 can be coupled to the distal end of the drainage conduit 112 (e.g., shown in FIGS. 1, 5 and 6), and the collection reservoir 114 is configured to contain the feces.

In this example, the collection reservoir 114 includes a port 2270 and a cap 2272. The port 2270 defines an opening 2274 in the collection reservoir 114 through which feces can be received from the drainage conduit 112. The cap 2272 is configured to removably couple to the port 2270 at the opening 2274. In particular, the cap 2272 is operable between (i) an open state in which the cap 2272 is decoupled from the port 2270 at the opening 2274 such the opening 2274 is uncovered by the cap 2272 (as shown in FIG. 22B), and (ii) a closed state in which the cap 2272 is coupled to the port 2270 at the opening 2274 such that the opening 2274 is covered by the cap 2272 (as shown in FIG. 22A). In this arrangement, the drainage conduit 112 can be coupled to the port 2270 to pass feces into the collection reservoir 114 when the cap 2272 is in the open state, and the cap 2272 can help to inhibit or prevent feces from leaking out of the opening 2274 of the port 2270 when the cap 2272 is in the closed state.

In FIGS. 22A-22B, the cap 2272 is coupled to an exterior surface of the port 2270 such that (i) the cap 2272 is movable between the open state and closed state, and (ii) the cap 2272 remains coupled to the port 2270 when the cap 2272 is in the open state. For instance, in FIGS. 22A-22B, the cap 2272 is coupled to the port 270 by a connector portion 2276. In one example, the connector portion 2276 can be living hinge. In another example, the connector portion 2276 can be a leash that extends between the cap 2272 and the port 2270. In some examples, the port 2270, the cap 2272, and the connector portion 2276 can be a monolithic structure. In other examples, one or more of the port 2270, the cap 2272, and the connector portion 2276 can be formed separate components that are later coupled to each other.

Additionally, in FIGS. 22A-22B, the cap 2272 includes a hook 2278. The hook 2278 can be configured to couple the collection reservoir 114 to a support structure (e.g., a hospital bed and/or wheel chair) while the cap 2272 is in the open state. This can help to hang and support the collection reservoir 114 while the drainage tube 112 is coupled to the port 2270.

Figure 23:
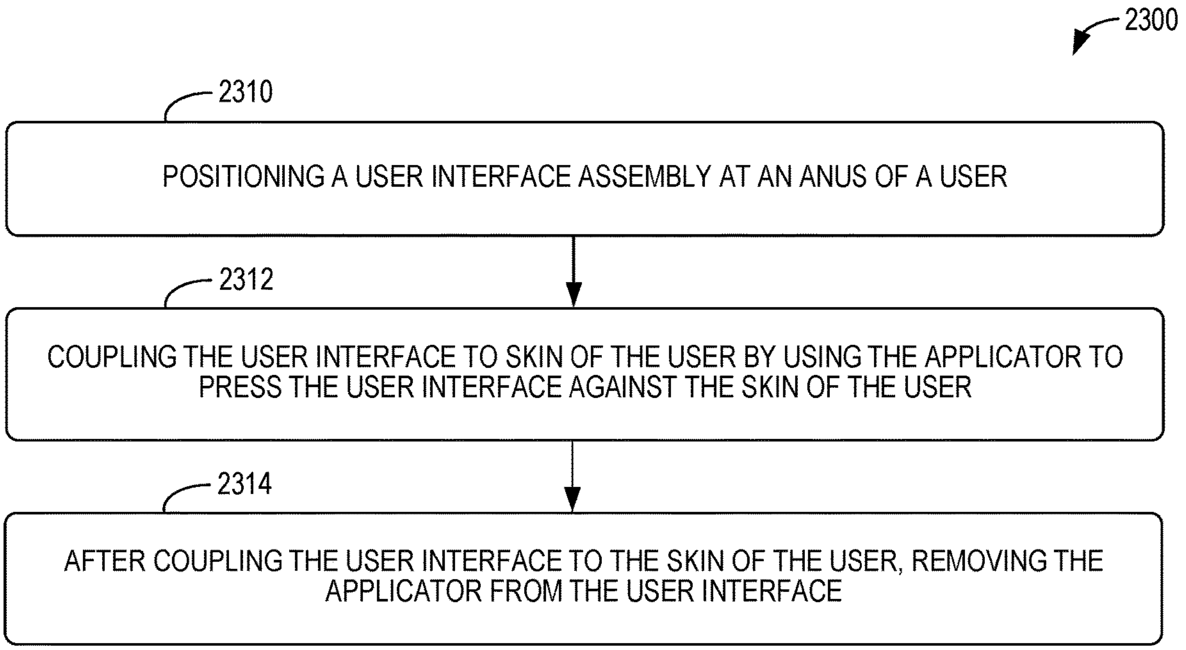
FIG. 23 depicts a flowchart for a process of using a fecal collection system according to an example.

Referring now to FIG. 23, a flowchart of a process 2300 for using a fecal collection system is shown according to an example. At block 2310, the process 2300 includes positioning a user interface assembly at an anus of a user. The user interface assembly includes a user interface and an applicator. At block 2312, the process 2300 includes coupling the user interface to skin of the user by using the applicator to press the user interface against the skin of the user. At block 2314, the process 2300 includes, after coupling the user interface to the skin of the user at block 2312, removing the applicator from the user interface.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A fecal collection system, comprising:

a user interface assembly, comprising:

a user interface having a proximal side and a distal side, wherein the proximal side is configured to couple to skin of a user, wherein the user interface comprises a first adhesive sheet and a second adhesive sheet, wherein the first adhesive sheet is coupled to the proximal side of the user interface, and the second adhesive sheet is coupled to a proximal side of the first adhesive sheet, wherein the second adhesive sheet comprises a plurality of apertures such that a portion of the first adhesive sheet is exposed through the plurality of apertures in the second adhesive sheet, and an applicator coupled to the distal side of the user interface, wherein the applicator is removable from the user interface while the user interface is coupled to the user;

a drainage conduit extending between a proximal end and a distal end, wherein the proximal end is configured to couple to the distal side of the user interface, wherein the drainage conduit defines a lumen configured to guide feces from the proximal end to the distal end; and a collection reservoir coupled to the distal end of the drainage conduit.

2. The fecal collection system of claim 1, wherein the first adhesive sheet and the second adhesive sheet define an aperture that is axially aligned with a lumen of the drainage conduit.

3. The fecal collection system of claim 1, further comprising a first one-way valve in the lumen defined by the drainage conduit, wherein the first one-way valve is configured to allow feces to flow in a direction from the proximal end to the distal end and inhibit the feces from flowing in a direction from the distal end to the proximal end.

4. The fecal collection system of claim 1, wherein the collection reservoir comprises a second one-way valve that is configured to allow feces to flow from the drainage conduit to the collection reservoir and inhibit the feces from flowing from the collection reservoir to the drainage conduit.

5. The fecal collection system of claim 1, wherein the applicator comprises a first lateral portion, a second lateral portion, and a hinge portion between the first lateral portion and the second lateral portion, and wherein the first lateral portion and the second lateral portion are configured to move about the hinge portion between an extended state and a folded state.

6. The fecal collection system of claim 5, wherein the applicator further comprises a slit extending along the hinge portion between the first lateral portion and the second lateral portion of the applicator.

7. The fecal collection system of claim 6, wherein the hinge portion comprises a first bridge portion and a second bridge portion, and wherein the first later portion and the second lateral portion are coupled to each other only at the first bridge portion and the second bridge portion.

8. The fecal collection system of claim 5, wherein the applicator comprises an alignment indicator that indicates a position of an aperture in the user interface, and wherein the alignment indicator comprises a first line that extends on the applicator from a top of the aperture to a peripheral edge of an adhesive sheet, and a second line that extends on the applicator from a bottom of the aperture to the peripheral edge of the adhesive sheet.

9. The fecal collection system of claim 1, wherein a proximal end of the drainage conduit is coupled to the user interface at a location that is offset below a center of the user interface.

10. The fecal collection system of claim 1, wherein the user interface further comprises a first release liner removably coupled to a first half of an adhesive sheet of the user interface; and a second release liner removably coupled to a second half of the adhesive sheet.

11. The fecal collection system of claim 10, wherein the first release liner comprises a first portion and a second portion, wherein the first portion of the first release liner covers the first half of the adhesive sheet, wherein the second portion of the first release liner has a first end that is coupled to the first portion of the first release liner at an inner portion of the user interface and a second end that is separate from the first portion of the first release liner at an outer portion of the user interface, wherein the second release liner comprises a first portion and a second portion, wherein the first portion of the second release liner covers the second half of the adhesive sheet, and wherein the second portion of the second release liner has a first end that is coupled to the first portion of the second release liner at an inner portion of the user interface and a second end that is separate from the first portion of the second release liner at an outer portion of the user interface.

12. The fecal collection system of claim 1, wherein the plurality of apertures are uniformly distributed over an entirety of the second adhesive sheet.

13. The fecal collection system of claim 1, wherein the first adhesive sheet has a first adhesive strength, and the second adhesive sheet has a second adhesive strength, which is different than the first adhesive strength.

14. The fecal collection system of claim 13, the first adhesive strength is greater than the second adhesive strength.

15. The fecal collection system of claim 13, the first adhesive strength is less than the second adhesive strength.

16. The fecal collection system of claim 1, wherein the collection reservoir comprises:

a port that defines an opening in the collection reservoir through which feces is receivable from the drainage conduit; and a cap removably coupled to the port at the opening, wherein the cap is operable between (i) an open state in which the cap is decoupled from the port at the opening such the opening is uncovered by the cap, and (ii) a closed state in which the cap is coupled to the port at the opening such that the opening is covered by the cap, wherein the cap comprises a hook that is configured to couple the collection reservoir to a support structure.

17. The fecal collection system of claim 16, wherein the cap is coupled to the port by a living hinge.

18. A method of using a fecal collection system, comprising:

positioning a user interface assembly of a fecal collection system at an anus of a user, wherein the fecal collection system comprises:

the user interface assembly, comprising:

(i) a user interface having a proximal side and a distal side, wherein the proximal side is configured to couple to skin of a user, wherein the user interface comprises a first adhesive sheet and a second adhesive sheet, wherein the first adhesive sheet is coupled to the proximal side of the user interface, and the second adhesive sheet is coupled to a proximal side of the first adhesive sheet, wherein the second adhesive sheet comprises a plurality of apertures such that a portion of the first adhesive sheet is exposed through the plurality of apertures in the second adhesive sheet, and (ii) an applicator coupled to the distal side of the user interface, wherein the applicator is removable from the user interface while the user interface is coupled to the user, a drainage conduit extending between a proximal end and a distal end, wherein the proximal end is configured to couple to the distal side of the user interface, wherein the drainage conduit defines a lumen configured to guide feces from the proximal end to the distal end, and a collection reservoir coupled to the distal end of the drainage conduit;

coupling the user interface to skin of the user by using the applicator to press the user interface against the skin of the user; and after coupling the user interface to the skin of the user, removing the applicator from the user interface.

19. The method of claim 18, wherein coupling the user interface to skin of the user comprises coupling the first adhesive sheet and the second adhesive sheet of the user interface to the skin of the user.

20. The method of claim 18, wherein coupling the user interface to the skin of the user by using the applicator to press the user interface against the skin of the user comprises:

hingedly moving a first lateral portion of the applicator and a second lateral portion of the applicator relative to each other to press the user interface against the skin of the user.

* * * * *